(12) United States Patent
Akutsu et al.

(10) Patent No.: US 7,145,658 B2
(45) Date of Patent: Dec. 5, 2006

(54) APPARATUS AND METHOD FOR EVALUATING SEMICONDUCTOR MATERIAL

(75) Inventors: Haruko Akutsu, Yokosuka (JP); Katsumi Rikimaru, Yokohama (JP); Kyoichi Suguro, Yokohama (JP); Tatsuya Shima, Yokohama (JP); Yoshimasa Kawase, Yokohama (JP); Atsushi Murakoshi, Oita (JP)

(73) Assignee: Kabushiki Kaisha Toshiba, Tokyo (JP)

(*) Notice: Subject to any disclaimer, the term of this patent is extended or adjusted under 35 U.S.C. 154(b) by 499 days.

(21) Appl. No.: 10/635,539

(22) Filed: Aug. 7, 2003

(65) Prior Publication Data
US 2004/0196464 A1  Oct. 7, 2004

(30) Foreign Application Priority Data
Apr. 3, 2003 (JP) .............................. 2003-100442

(51) Int. Cl.
*G01N 21/41* (2006.01)
(52) U.S. Cl. ..................................... 356/432; 356/445
(58) Field of Classification Search ........ 356/432–440, 356/445–448; 250/341.1, 339.11, 360.1; 438/16
See application file for complete search history.

(56) References Cited

U.S. PATENT DOCUMENTS

| 4,652,757 | A | * | 3/1987 | Carver .................... 250/360.1 |
|---|---|---|---|---|
| 4,750,822 | A | * | 6/1988 | Rosencwaig et al. ........ 356/445 |
| 4,904,902 | A | * | 2/1990 | Tamai et al. ............. 315/111.81 |
| 6,049,220 | A | | 4/2000 | Borden et al. |
| 6,323,951 | B1 | | 11/2001 | Borden et al. .............. 356/502 |
| 6,917,039 | B1 | * | 7/2005 | Nicolaides et al. ....... 250/341.1 |
| 2003/0234933 | A1 | * | 12/2003 | Nicolaides et al. ......... 356/445 |
| 2004/0174529 | A1 | | 9/2004 | Maznev et al. |
| 2004/0253751 | A1 | * | 12/2004 | Salnik et al. .................. 438/16 |
| 2005/0062971 | A1 | * | 3/2005 | Salnik et al. ................ 356/432 |

FOREIGN PATENT DOCUMENTS

| JP | 63-155628 | 6/1988 |
|---|---|---|
| JP | 6-318560 | 11/1994 |
| JP | 410255714 A * | 9/1998 |

OTHER PUBLICATIONS

First Notification of Reason for Refusal issued by Taiwanese Patent Office, mailed Apr. 25, 2005, in Taiwanese Application No. 093109303, and English-language translation thereof.
Notice of Grounds for Rejection issued by the Japanese Patent Office mailed Apr. 18, 2006, for Japanese Patent Application No. 2003-100442, and English-language translation thereof.

* cited by examiner

*Primary Examiner*—Hoa Q. Pham
(74) *Attorney, Agent, or Firm*—Finnegan, Henderson, Farabow, Garrett & Dunner, L.L.P.

(57) ABSTRACT

An apparatus for evaluating semiconductor material having a pump laser configured to irradiate a pump beam modulated at a modulation frequency on a semiconductor wafer, a probe laser configured to irradiate a probe beam on the semiconductor wafer, and a detector configured to detect a reflection of the probe beam from the semiconductor wafer.

4 Claims, 22 Drawing Sheets

FIG. 21

| OXIDE FILM THICKNESS | IONIC SPECIES | ACCELERATION ENERGY | DOSE | ANGLE | ION IMPLANTER | IN-PLANE UNIFORMITY OF SIGNAL STRENGTH CONVERTED INTO DOSE (%) STANDARD DEVIATION (DOSE) % |
|---|---|---|---|---|---|---|
| 8nm | P | 500keV | 5E+13 | +2° | C | 0.65 |
| 8nm | P | 500keV | 5E+13 | PARALLEL | C | 0.38 |
| 8nm | P | 500keV | 5E+13 | -2° | C | 0.51 |
| 8nm | P | 500keV | 5E+13 | -5° | C | 2.42 |

FIG. 22

| IONIC SPECIES | ACCELERATION ENERGY | DOSE | ANGLE | ION IMPLANTER | IN-PLANE UNIFORMITY OF SIGNAL STRENGTH CONVERTED INTO DOSE (%) STANDARD DEVIATION (DOSE) % |
|---|---|---|---|---|---|
| B | 3keV | 3E+15 | '+2° | A | 0.483694052 |
| B | 3keV | 3E+15 | PARALLEL | A | 0.602034279 |
| B | 3keV | 3E+15 | '-2° | A | 0.633528518 |

FIG. 23

| TILT ANGLE | TWIST ANGLE | IN-PLANE UNIFORMITY IN DOSE (%) |
|---|---|---|
| 0 | 0 | 1.01 |
| 0 | 0 | 1.35 |
| 7 | 0 | 1.24 |
| 5 | 180 | 1.36 |
| 7 | 180 | 1.77 |
| 9 | 180 | 2.71 |
| 7 | 203 | 1.40 |
| 5 | 210 | 0.874 |
| 5 | 225 | 1.16 |
| 5 | 240 | 0.913 |
| 7 | 247 | 2.75 |
| 5 | 255 | 0.54 |
| 5 | 270 | 0.60 |
| 7 | 270 | 1.43 |

← ION BEAM AND WHEEL ROTATION AXIS ARE PARALLEL

← IMPLANTING CONDITIONS TO REDUCE CIRCUMFERENTIAL ANGULAR VARIATIONS

FIG. 24

| OXIDE FILM THICKNESS | IONIC SPECIES | ACCELERATION ENERGY | DOSE | ANGLE | ION IMPLANTER | IN-PLANE UNIFORMITY OF SIGNAL STRENGTH CONVERTED INTO DOSE (%) STANDARD DEVIATION (DOSE) % |
|---|---|---|---|---|---|---|
| 8nm | B | 30 | 1E+15 | 2° | B | 1.39 |
| 8nm | B | 30 | 1E+15 | PARALLEL | B | 1.34 |
| 8nm | B | 30 | 1E+15 | -2° | B | 1.10 |
| 8nm | B | 30 | 1E+15 | -5° | B | 0.92 |

# APPARATUS AND METHOD FOR EVALUATING SEMICONDUCTOR MATERIAL

CROSS REFERENCE TO RELATED APPLICATIONS

This application is based upon and claims the benefit of priority from the prior Japanese Patent Application P2003-100442 filed on Apr. 3, 2003; the entire contents of which are incorporated herein by reference.

BACKGROUND OF THE INVENTION

1. Field of the Invention

The present invention relates to an apparatus for and a method of evaluating semiconductor material. In particular, it relates to an apparatus for and a method of evaluating processes such as an ion implantation process conducted on semiconductor substrates through inspection of crystal defects caused in the semiconductor substrates due to the processes.

2. Description of Related Art

To form integrated circuits on a semiconductor wafer, the wafer is passed through a series of processes including an ion implantation process that implants ions, charged atoms or charged molecules in the wafer. During ion implantation, the implanted ions collide with crystal lattices in the wafer, causing point defects such as interstitial-atoms and vacancies. There are related arts for inspecting crystal defects in the wafer before and after ion implantation and evaluating various characteristics of the wafer according to a result of the inspection.

One of the such related arts irradiates a pump beam on an ion-implanted semiconductor wafer, the pump beam having energy equal to or larger than a bandgap width of the wafer. Some photons in the pump beam are absorbed by the wafer and generate photocarriers each consisting of a pair of a hole and an electron in the wafer. The related art irradiates a probe beam on the wafer, catches a reflected probe beam from the wafer, and from the reflected probe beam, reads a recombination process of the photocarriers in the wafer. The recombination process of excess carriers including the photocarriers depends on a crystallographic state in the wafer, and therefore, reading the recombination process results in reading the quantity of impurities implanted in the wafer, the depth of a preamorphous region in the wafer, and an after-annealing junction depth in the wafer.

The excess carriers in the semiconductor wafer caused by the pump beam recombine at a certain time constant. Due to the pump beam, point defects in the wafer move or annihilate to change the spatial distributions and concentration profile of the point defects during measurement and affect the recombination process of the excess carriers. Also, the intensity of the reflected probe beam varies depending on a measuring time, making it difficult to correctly measure the characteristics of the wafer. This problem becomes serious when a modulation frequency of kilohertz order is applied to the pump beam that pumps photocarriers in the wafer.

When the surface of the semiconductor wafer has a film of, for example, chemical oxide with much trapped charge, the film will change the intensity and phase of a reflected pump beam by several tens of percent.

SUMMARY OF THE INVENTION

A first aspect of the present invention provides an apparatus for evaluating semiconductor material having a pump laser configured to irradiate a pump beam modulated at a modulation frequency on a semiconductor wafer, a probe laser configured to irradiate a probe beam on the semiconductor wafer, and a detector configured to detect a reflection of the probe beam from the semiconductor wafer.

A second aspect of the present invention provides a method for evaluating semiconductor material having reducing charge trapped in a surface of a semiconductor wafer, implanting ions in the semiconductor wafer, and while irradiating a probe beam and a modulated pump beam on the semiconductor wafer, measuring an intensity of a reflection of the probe beam from the semiconductor wafer.

A third aspect of the present invention provides a method for evaluating semiconductor material having implanting ions in a semiconductor wafer placed on a wheel of a mechanical scan type ion implanter in a direction substantially parallel to a rotation axis of the wheel, and while irradiating a probe beam and a modulated pump beam on the semiconductor wafer, measuring an intensity of a reflection of the probe beam from the semiconductor wafer.

A fourth aspect of the present invention provides a method for evaluating semiconductor material having irradiating a pump beam modulated at a modulation frequency on a semiconductor wafer, irradiating a probe beam on the semiconductor wafer, and after irradiating the pump beam on the semiconductor wafer for at least three seconds, measuring an intensity of a reflection of the probe beam from the semiconductor wafer while irradiating the pump beam and probe beam on the semiconductor wafer.

A fifth aspect of the present invention provides a method for evaluating semiconductor material having irradiating a pump beam modulated at a modulation frequency on a semiconductor wafer, irradiating a probe beam on the semiconductor wafer, measuring an intensity of a reflection of the probe beam from the semiconductor wafer while irradiating the pump beam and probe beam on the semiconductor wafer, and generating a beam equivalent to the reflection in the same optical path as that of the reflection during a period in which no probe beam is being irradiated on the semiconductor wafer.

A sixth aspect of the present invention provides a method for evaluating semiconductor material having irradiating a pump beam modulated at a modulation frequency on a semiconductor wafer, irradiating a probe beam on the semiconductor wafer, measuring an intensity of a reflection of the probe beam from the semiconductor wafer while irradiating the pump beam and probe beam on the semiconductor wafer, finding a first functional form indicating a relation between a first elapsed time period from a time when ions were implanted into the semiconductor wafer to a time when the intensity of the reflection was measured and intensity changes of the reflection, and finding an intensity of the reflection just after the ions were implanted into the semiconductor wafer according to the intensity of the reflection measured, the first elapsed time period, and the first functional form.

A seventh aspect of the present invention provides a method for evaluating semiconductor material having implanting ions in a semiconductor wafer, while irradiating a probe beam and a pump beam modulated at a modulation frequency on the semiconductor wafer, measuring an intensity of a reflection of the probe beam from the semiconductor wafer, selectively extracting a double frequency component having a frequency being twice as large as the modulation frequency from the intensity of the reflection, measuring a phase shift between the double frequency component and a reference modulation component, and determining whether or not a topmost surface of the semiconductor wafer involves an amorphous state according to the phase shift measured.

A eighth aspect of the present invention provides a method for evaluating semiconductor material having implanting ions in a semiconductor wafer, while irradiating a probe beam and a pump beam modulated at a modulation frequency on the semiconductor wafer, measuring an intensity of a reflection of the probe beam from the semiconductor wafer, measuring a distribution of the intensity over a surface of the semiconductor wafer, and determining whether or not a topmost surface of the semiconductor wafer involves an amorphous state according to the distribution.

BRIEF DESCRIPTION OF THE DRAWINGS

FIG. 21 is a table showing various angles between an ion beam and a rotation axis of a wheel and corresponding values indicative of in-plane uniformity of signal strengths according to a first example of ion implantation;

FIG. 22 is a table showing various angles between an ion beam and a rotation axis of a wheel and corresponding values indicative of in-plane uniformity of signal strengths according to a second example of ion implantation;

FIG. 23 is a table showing tilt angles, twist angles, and corresponding values indicative of in-plane uniformity of signal strengths according to a third example of ion implantation;

FIG. 24 is a table showing various angles between an ion beam and a rotation axis of a wheel and corresponding values indicative of in-plane uniformity of signal strengths according to the third example of ion implantation;

DETAILED DESCRIPTION OF EMBODIMENTS

Figure 1:
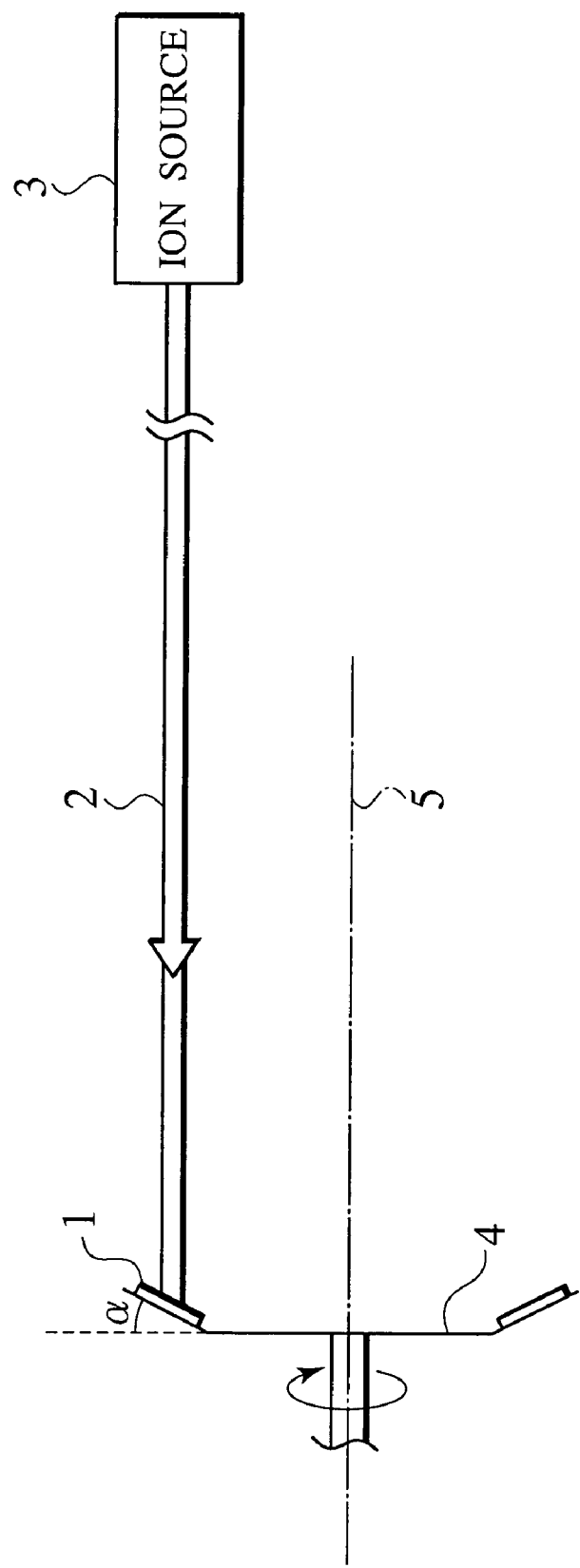
FIG. 1 is a sectional view showing an ion implanter according to an embodiment of the present invention.

Various embodiments of the present invention will be described with reference to the accompanying drawings. It is to be noted that the same or similar reference numerals are applied to the same or similar parts and elements throughout the drawings, and the description of the same or similar parts and elements will be omitted or simplified.

As shown in FIG. 1, the ion implanter has a wheel 4 on which a plurality of semiconductor wafers (hereinafter referred to simply as the wafers) 1 are placed and an ion source 3 generating ions to be implanted in the wafers 1. The wheel 4 has a pan shape with a flat bottom and is turned around a rotation axis 5. A peripheral side wall of the wheel 4 is inclined by a given angle α relative to a plane orthogonal to the rotation axis 5. The wafers 1 are set on the inclined periphery of the wheel 4. The ion source 3 emits ions in an ion beam 2. The ion beam 2 having a uniform velocity, being oriented in a given direction, is implanted in each wafer 1. The ion implanter of FIG. 1 is of a mechanical scan type that turns the wheel 4 with the wafers 1 around the rotation axis 5, so as to uniformly implant ions in the surface of each of the wafers 1.

The ion beam 2 is substantially in parallel with the rotation axis 5 of the wheel 4. More precisely, the ion beam 2 is in parallel with the rotation axis 5, or forms an angle of 2.5 degrees or less relative to the rotation axis 5. The angle is determined according to acceleration energy of the ion beam 2, a crystal plane of the wafer 1, ionic species, channeling conditions, and the like.

Figure 2:
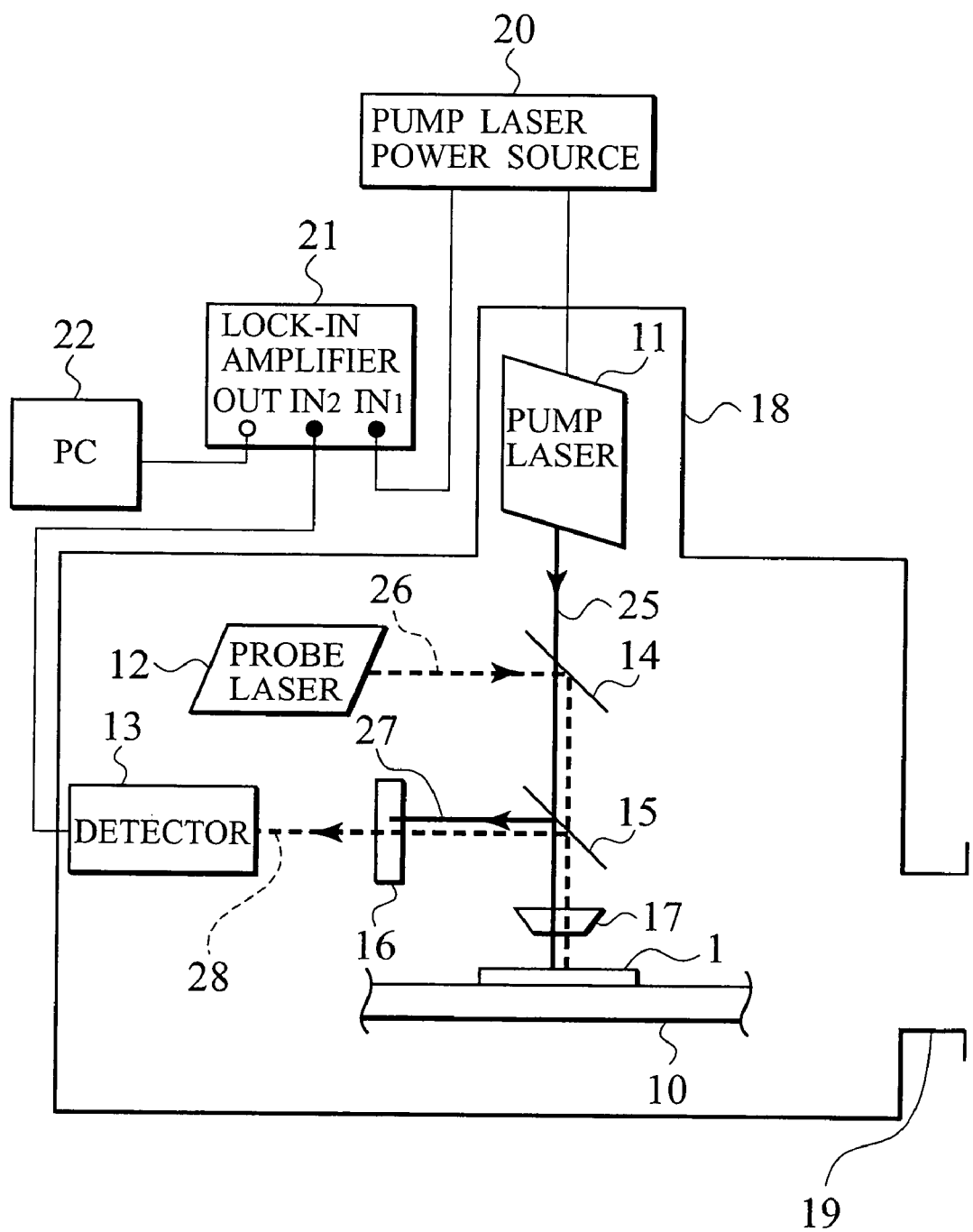
FIG. 2 is a block diagram showing an apparatus for evaluating semiconductor material according to an embodiment of the present invention.

In FIG. 2, an apparatus for evaluating semiconductor material according to an embodiment of the present invention is shown. The apparatus evaluates various characteristics of each wafer 1 into which the ion implanter of FIG. 1 has implanted ions. The wafer characteristics to be evaluated include an implanted ion dose, an implanted ion depth, a preamorphous layer thickness, a junction depth, a crystal defect concentration, and the like. Components of the apparatus of FIG. 2 will be explained. A stage 10 receives one of the wafers 1 shown in FIG. 1. A pump laser 11 emits a pump beam 25 toward the wafer 1. A probe laser 12 emits a probe beam 26 toward the wafer 1. A filter 16 absorbs a reflected pump beam from the surface or the inside of the wafer 1 and transmits a reflected probe beam 28 from the surface or the inside of the wafer 1. A detector 13 detects the reflected probe beam 28 transmitted through the filter 16. A first half-mirror 14 reflects the probe beam 26, to make the probe beam 26 coaxial with the pump beam 25. A second half-mirror 15 reflects the reflected probe beam 28 toward the detector 13. An objective lens 17 focuses the pump beam 25 and probe beam 26 on the surface of the wafer 1. A chamber 18 accommodates the stage 10, pump laser 11, probe laser 12, filter 16, detector 13, first and second half-mirrors 14 and 15, and objective lens 17. A load port 19 is formed at a part of the chamber 18. A pump laser power source 20 is connected to the pump laser 11. A lock-in amplifier 21 is connected to the power source 20 and the detector 13. A computer (PC) 22 is connected to the lock-in amplifier 21.

The pump beam 25 from the pump laser 11 passes through the first and second half-mirrors 14 and 15 and objective lens 17 and irradiates the wafer 1. The pump laser 11 periodically modulates the intensity of the pump beam 25. Part of the probe beam 26 from the probe laser 12 is reflected by the first half-mirror 14, is passed through the objective lens 17, and irradiates the wafer 1. The probe beam 26 from the probe laser 12 has a fixed intensity and is not modulated. Part of the reflected pump beam 27 is reflected by the second half-mirror 15 and is absorbed by the filter 16. Part of the reflected probe beam 28 is reflected by the second half-mirror 15, is transmitted through the filter 16, and is detected by the detector 13. The detector 13 converts the detected beam 28 into an electric signal and transmits the electric signal to the lock-in amplifier 21. The strength of the electric signal from the detector 13 corresponds to the intensity of the reflected probe beam 28.

The pump laser power source 20 supplies power to operate the pump laser 11 and a modulation frequency to determine a modulation period of the intensity of the pump beam25. The lock-in amplifier 21 lock-in-amplifies the signal from the detector 13 in synchronization with the modulation frequency applied to the pump beam 25 by the pump laser power source 20 and transfers the amplified signal to the computer 22. The computer 22 corrects the strength of the lock-in-amplified signal and finds a strength of the signal just after ions were implanted. The chamber 18 blocks optical noise interfering with optical measurement. The load port 19 is used to take the wafer 1 into and out of the chamber 18.

Figure 3:
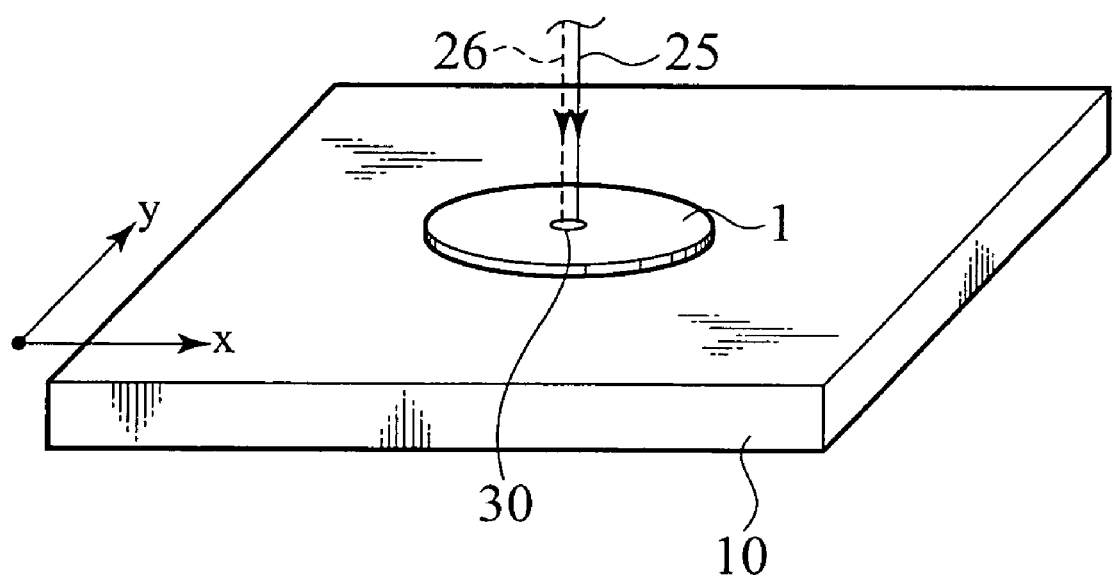
FIG. 3 is a perspective view showing an area irradiated with a pump beam and probe beam on a stage of the apparatus of FIG. 2.

In FIG. 3, the pump beam 25 and probe beam 26 emitted to an irradiation area 30 on the wafer 1 on the stage 10 are shown. The pump laser 11, probe laser 12, filter 16, detector 13, first and second half-mirrors 14 and 15, and objective lens 17 shown in FIG. 2 are fixed relative to the chamber 18.

In FIG. 3, the stage 10 is movable in orthogonal x and y directions in a plane orthogonal to the optical axes of the pump beam 25 and probe beam 26. The stage 10 is moved to set the irradiation area 30 to an optional position on the stage 10.

Figure 4:
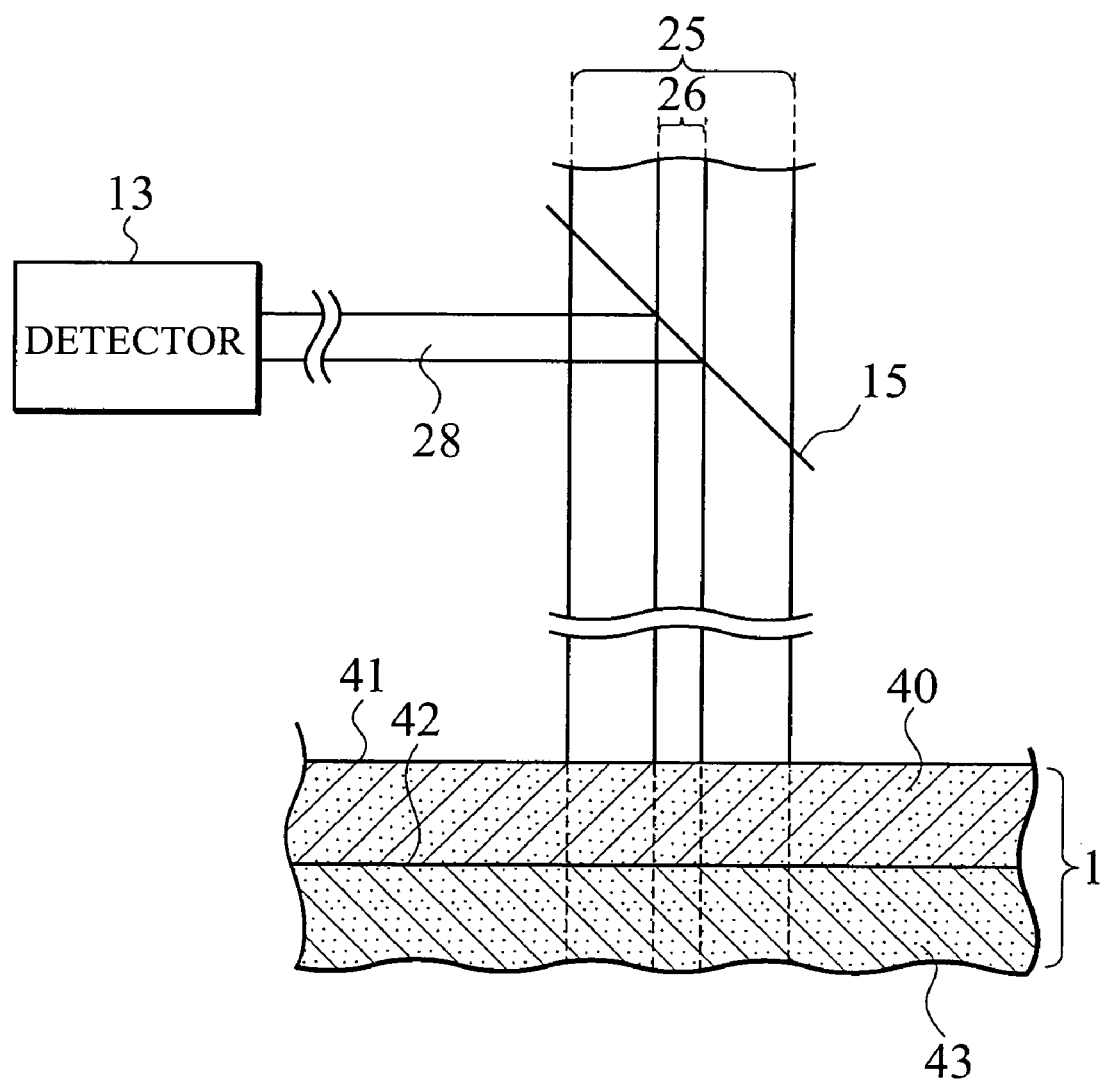
FIG. 4 is an enlarged sectional view showing a semiconductor wafer irradiated with a pump beam and probe beam in the apparatus of FIG. 2.

By referencing to FIGS. 4 to 6, measuring principles of the apparatus of FIGS. 2 and 3 will be explained. In FIG. 4, the pump beam 25 is a laser beam of, for example, 2 kHz in modulation frequency and 830 nm in wavelength $\lambda 1$ irradiated on the surface 41 of the wafer 1. The probe beam 26 is a laser beam of, for example, 980 nm in wavelength $\lambda 2$ without intensity modulation irradiated on the surface 41 of the wafer 1. The pump beam 25 has a photon energy of about 1.5 eV and the probe beam 26 has a photon energy of about 1.26 eV. Each of these energy values is greater than a bandgap width (1.12 eV) of monocrystalline silicon (Si). After passing 14 μm in the monocrystalline silicon wafer 1, the pump beam 25 reduces its intensity to 1/e (about 0.37) of the original intensity. On the other hand, after passing 65 μm in the wafer 1, the probe beam 26 whose photon energy is smaller than that of the pump beam 25 reduces its intensity to 1/e of the original intensity. Generally, the intensity of the probe beam 26 attenuates only by 1.5% after advancing to a depth of 1 μm from the surface 41 of the wafer 1 in an ion implanted region 40. On the other hand, the intensity of the pump beam 25 attenuates by 7% after advancing to a depth of 1 μm from the surface 41 of the wafer 1 in the ion implanted region 40. The attenuated part of the pump beam 25 is absorbed in the wafer 1. As mentioned above, the photon energy of the pump beam 25 is greater than the bandgap of silicon, and therefore, the pump beam 25 absorbed in the wafer 1 pumps excess carriers each consisting of a pair of an electron and a hole. The excess carriers pumped in the wafer 1 by the pump beam 25 are hereinafter referred to as the "photocarriers." The pump beam 25 irradiated on the wafer 1 has photon energy equal to or greater than the bandgaps width of the semiconductor material that forms the wafer 1. The pump beam 25 absorbed in the wafer 1 pumps photocarriers in the wafer 1.

The implanted ions in the wafer 1 damage or reform a crystal structure in the ion implanted region 40, thereby deteriorating the crystalline perfection of the region 40. Therefore, excess carriers including photocarriers in the region 40 have a relatively short life time before annihilation and quickly recombine. On the other hand, a region (no-ion implanted region) 43 deeper than the ion implanted region 40 has good crystalline characteristics because the implanted ions do not easily reach the no-ion implanted region 43. In the no-ion implanted region 43, the life time of excess carriers is relatively long, and therefore, a concentration of excess carriers is high therein. Namely, the irradiated pump beam 25 causes a sudden change in an excess carrier distribution along a boundary plane 42 between the ion implanted region 40 and the no-ion implanted region 43. In terms of optics, a light refractive index suddenly changes at the boundary plane 42. Reflectivity of the probe beam 26 locally increases at the boundary plane 42 at a maximum changing rate of refractive index. Consequently, the probe beam 26 is reflected at the surface 41 of the wafer 1 as well as at the boundary plane 42 of the wafer 1. The reflected probe beam 28, therefore, contains a first reflected beam from the surface 41 and a second reflected beam from the boundary plane 42.

The first and second reflected beams interfere with each other, and the phase of the reflected probe beam 28 shifts from the phase of the pump beam 25. The reflected probe beam 28 is reflected by the second half-mirror 15 toward the detector 13, which converts the reflected probe beam 28 into an electric signal.

The strength of the electric signal depends on a concentration profile of crystal defects caused by the implanted ions and a concentration profile of the implanted ions. The apparatus of FIGS. 2 and 3 finds a relationship between signals and doses of the implant, and converts the detected signal into the dose. Therefore, the apparatus of FIGS. 2 and 3 evaluates the characteristics of the wafer 1, such as the dose, a projected range, a preamorphous layer thickness, a pn junction depth after heat treatment, and a crystal defect concentration related to the wafer 1. The apparatus of FIGS. 2 and 3 uses the reflected probe beam 28, to read a recombination process of photocarriers pumped by the pump beam 25. The recombination process of photocarriers depends on a crystallographic state in the wafer 1, and therefore, can be used to read information about impurities introduced in the wafer 1, an amorphous region thickness in the wafer 1, and a junction depth in the wafer 1.

The intensity of the second reflected beam from the boundary plane 42 in the wafer 1 is smaller than that of the first reflected beam from the surface 41 of the wafer 1. When the pump beam 25 is continuously irradiated at a given intensity, the first reflected beam from the surface 41 and the second reflected beam from the boundary plane 42 remain at a constant intensity, it is substantially impossible to measure a change in the second reflected beam from the boundary plane 42.

Figure 5:
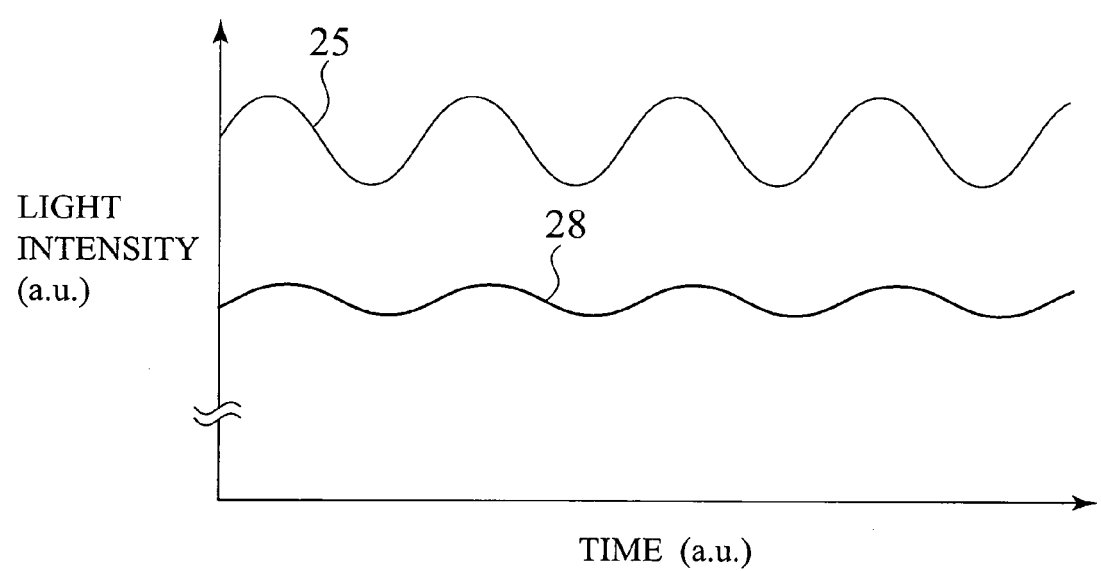
FIG. 5 is a graph showing the intensities of a modulated pump beam and reflected probe beam.
Figure 6:
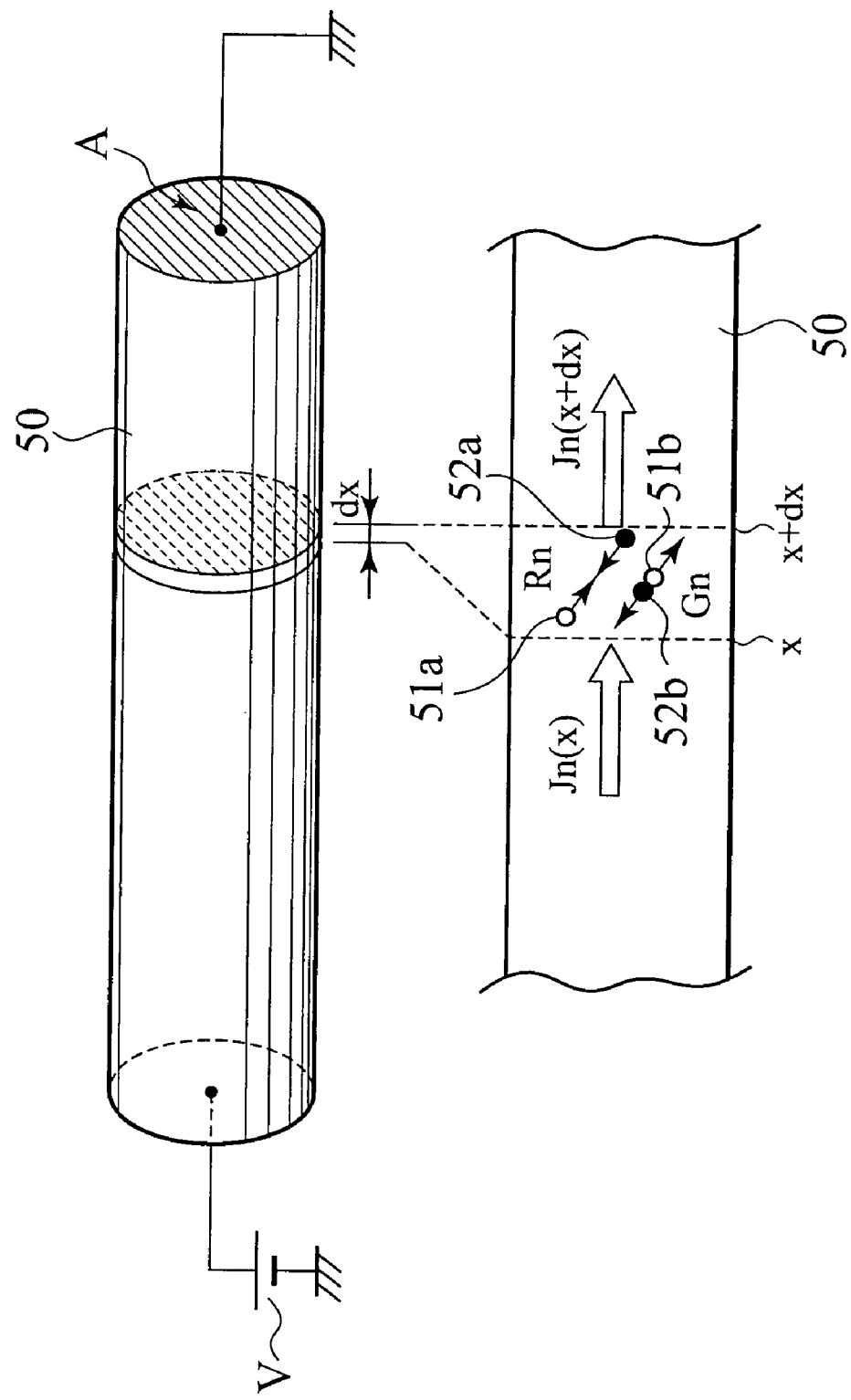
FIG. 6 is a model showing the behaviors of excess carriers in a semiconductor current path made of p-type monocrystalline silicon.

Therefore, as shown in FIG. 5, the intensity of the pump beam 25 irradiated on the wafer 1 is periodically modulated by adding a modulation component to a constant DC component. Then, the generation of excess carriers changes temporally. The intensity of the reflected probe beam 28 periodically changes at the modulation period of the pump beam 25, to have phases corresponding to the generation of excess carriers. By lock-in-amplifying and reading changes in the reflected probe beam 28 synchronized with the modulation period of the pump beam 25, it is possible to selectively extract a component indicative of photocarrier generation from the reflected probe beam 28.

By referring to the FIG. 6, the behaviors of excess carriers 51a, 51b, 52a, and 52b generated in a semiconductor current path 50 made of p-type monocrystalline silicon and having a cross-sectional area A will be explained. When a voltage V is applied to the ends of the current path 50, a current density $J_n(x)$ due to electrons is as follows:

$$J_n(x) = q\mu_n N_p E + q D_n (\partial N_p / \partial x) \quad (1)$$

where q is the magnitude of electronic charge, $\mu_n$ the electron mobility, $N_p$ the electron concentration in the conduction band in the semiconductor current path 50, E the electric field ($E = \partial V/\partial x$), and $D_n$ the electron diffusion coefficient.

The time derivative of the electron concentration per unit volume (Adx) is expressed as follows:

$$\frac{\partial N_p}{\partial t} = \frac{1}{q}\frac{\partial J_n}{\partial x} + (G_n - R_n) \quad (2)$$

where $G_n$ is the generation rate of the holes 51a and 51b and electrons 52a and 52b and $R_n$ is the recombination rate of the holes 51a and 51b and electrons 52a and 52b.

When there is no electric field (E=0), the first term of the right side of the expression (1) can be ignored. By substituting the right side of the expression (1) for the first term of the right side of the expression (2), the following is obtained:

$$\frac{\partial N_p}{\partial t} = D_n \frac{\partial^2 N_p}{\partial x^2} + G_n - \frac{N_p - N_{p0}}{\tau_n} \quad (3)$$

where $N_{p0}$ is the electron concentration without the pump beam 25 and $\tau_n$ is the life time of the electrons 52a and 52b in p-type monocrystalline silicon.

When the electron concentration changes at an angular frequency ω, the expression (3) will be modified as follows:

$$\frac{\partial^2 N_p}{\partial x^2} - N_p\left(\frac{1}{D_n\tau_n} + i\frac{\omega}{D_n}\right) + \left(\frac{G_n}{D_n} + \frac{N_{p0}}{D_n\tau_n}\right) = 0 \quad (4)$$

The life time $\tau_n$ of the electrons 52a and 52b is about 1.0 μs, and a reciprocal of the life time $\tau_n$ is $1/\tau_n = 1$ MHz. When the modulation frequency ω/2π of the pump beam 25 is 2 kHz, the reciprocal of the life time $\tau_n$ is sufficiently larger than the modulation frequency of the pump beam 25. Accordingly, the third term of the left side of the expression (4) provides substantially no effect, and a spatial distribution of excess carriers becomes steady and temporally unchangeable. When the modulation frequency of the pump beam 25 is about 1 MHz, the third and fourth terms of the left side of the expression (4) equally contribute to determining an excess carrier spatial distribution. Namely, the excess carrier spatial distribution temporally changes.

A method of lowering the modulation frequency ω/2π of the pump beam 25 to a negligible level relative to the reciprocal of the life time $\tau_n$ of the electrons 52a and 52b is hereunder referred to as "the first semiconductor material evaluation method". A method of setting the modulation frequency ω/2π of the pump beam 25 to a level equivalent to the reciprocal of the life time $\tau_n$ of the electrons 52a and 52b is hereunder referred to as "the second semiconductor material evaluation method". The apparatus shown in FIG. 2 and 3 preferably employs the first semiconductor material evaluation method. The apparatus shown in FIG. 2 and 3, however, is not limited to employ the first semiconductor material evaluation method, it can also employs the second semiconductor material evaluation method.

Figure 7:
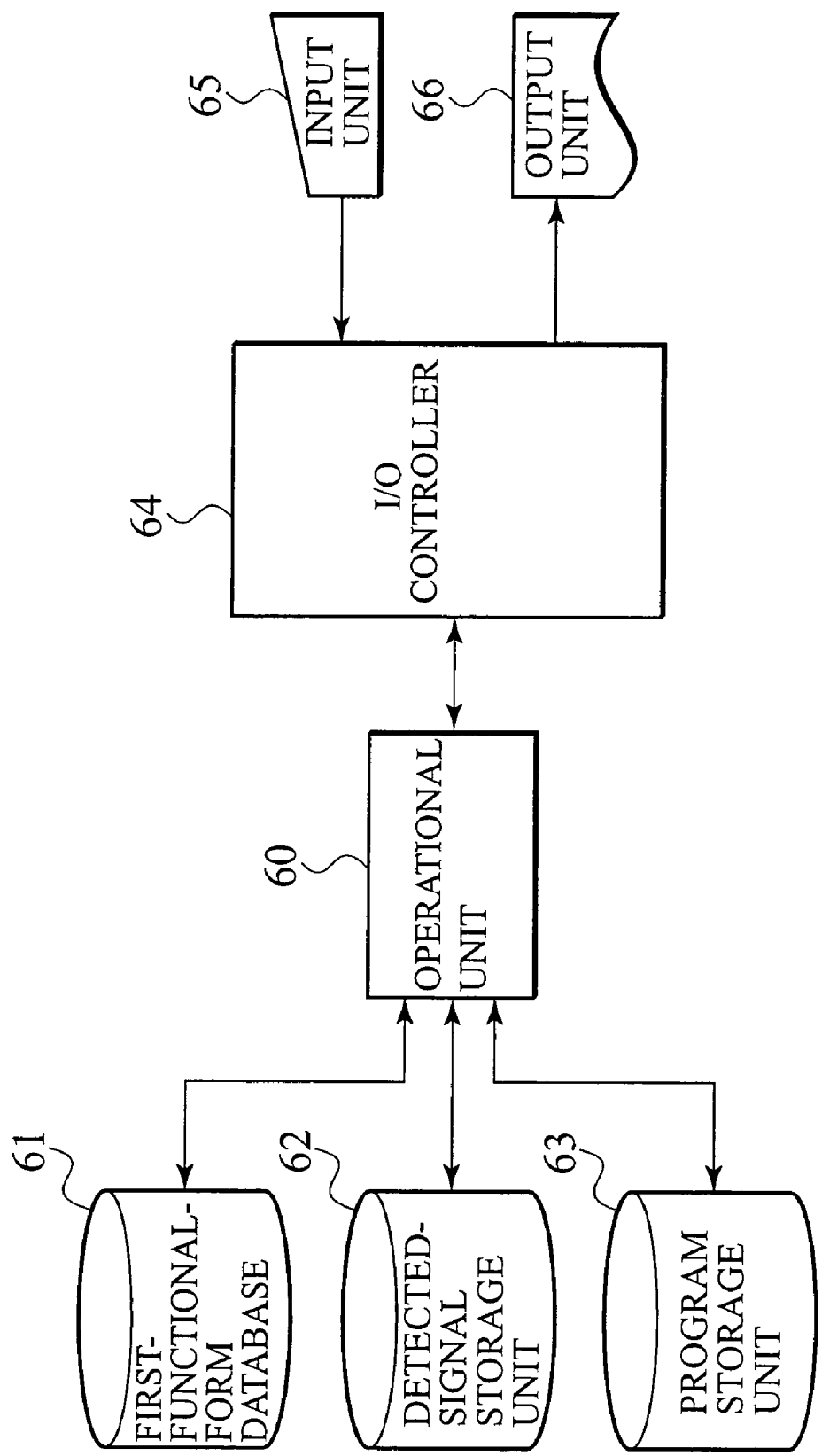
FIG. 7 is a block diagram showing a computer associated with the apparatus of FIG. 2.

By referencing to FIG. 7, the computer 22 of FIG. 2 will be explained. The computer 22 has an operational unit 60 having a function of correcting a signal from the lock-in amplifier 21 of FIG. 2, a first functional form database 61, a detected signal storage unit 62, and a program storage unit 63. The first functional form database 61, the detected signal storage unit 62 and the program storage unit 63 are connected to the operational unit 60.

The operational unit 60 implements a part of a central processing unit (CPU) of the computer 22. Although not shown in FIG. 7, the operational unit 60 includes a main storage unit to temporarily store a computer readable program to correct signals and data to be processed by the operational unit 60. The first functional form database 61, detected signal storage unit 62, and program storage unit 63 may be semiconductor memories such as ROMs and RAMs, or auxiliary storage units such as magnetic disk units, magnetic drum units, and magnetic tape units. Alternatively, they may be parts of the main storage unit in the CPU. The operational unit 60 is connected to an input unit 65 and an output unit 66 through an I/O controller 64. The input unit 65 receives data and instructions from an operator, and the output unit 66 provides the corrected signals. The input unit 65 may include a barcode input unit, keyboard, mouse, light pen, and flexible disk unit. The output unit 66 may include a display and printer.

The first functional form database 61 stores first functional forms indicating signal strength changes relative to the time elapsed from ion implantation. The details of the first functional forms will be explained later with reference to FIG. 8. The detected signal storage unit 62 stores information about signals from the lock-in amplifier 21 of FIG. 2, the elapsed time period from the start of irradiation of the pump beam 25 to the intensity measurement of the reflected probe beam 28, and the elapsed time period from ion implantation to intensity measurement of the reflected probe beam 28. The program storage unit 63 stores program instructions executed by the operational unit 60. The operational unit 60 finds a signal strength just after ion implantation according to information stored in the storage unit 62 and the first functional form retrieved from the first functional form database 61.

By referencing to FIG. 8, an example of a profile of a first functional form f1 stored in the database 61 will be explained. An abscissa indicates elapsed period from the time of the ion implantation and an ordinate indicates signal strength. The signal strength decreases according to the interval elapsed from the time of the ion implantation. More precisely, the signal strength steeply decreases just after ion implantation and stabilizes as the time interval elapsed from ion implantation extends. The profile of a first functional form f1 depends on ion implanting conditions and the irradiation periods of the pump beam 25 and probe beam 26. A signal strength Sga1 is a value actually measured at time t1. A signal strength Sga0 is an estimated value just after ion implantation, provided through correction by the operational unit 60.

The first functional form f1 is expressed as follows by adding up a plurality of terms including logarithms of the time elapsed from ion implantation:

$$f1 = f0 + C_1 \exp(-t/\tau_1) + C_2 \exp(-t/\tau_2) + \Sigma C_k \exp(-t/\tau_k) \quad (5)$$

where f0, $C_1$, $C_2$, $C_k$, $\tau_1$, $\tau_2$, $\tau_k$ are correction coefficients. These correction coefficients are obtainable by measuring signals at different elapsed time periods after ion implantation with the use of the apparatus of FIG. 2. The correction coefficients of the first functional form f1 vary according as the ion implanting conditions and the irradiation periods of the pump beam 25 and probe beam 26. Generally, the first functional form f1 is sufficiently expressible only with the first to third terms of the right side of the expression (5), and the fourth term thereof may be added if required.

By referencing to FIGS. 9 to 11, semiconductor wafer processing and evaluation processes carried out by using the mechanical scan type ion implanter of FIG. 1 and the apparatus of FIG. 2 will be explained.

Figure 9:
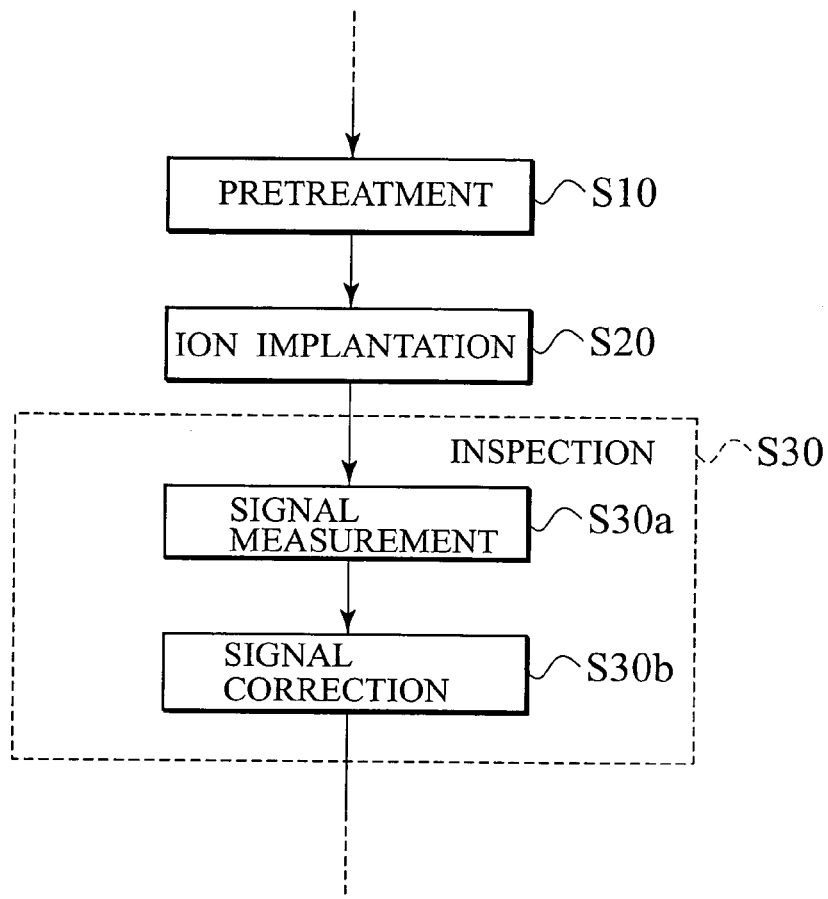
FIG. 9 is a general flowchart showing a flow of semiconductor wafer processes according to an embodiment of the present invention.

(1) Stage S10 of FIG. 9 carries out a pretreatment process before implanting ions in the wafer 1. The details of the pretreatment process will be explained with reference to FIG. 10.

(2) Stage S20 implant ions in the wafer 1 using the mechanical-scan-type ion implanter of FIG. 1. At this time, an ion implanting angle is properly selected according to ion implanting recipe, and the ion beam 2 is emitted substantially in parallel with the rotation axis 5 of the wheel 4.

(3) Stage S30 inspects and evaluates the characteristics of the wafer 1 processed in stage S20. Stage S30 includes stage S30a that measures signals using the optical system of the apparatus of FIG. 2, and stage S30b that corrects the measured signals using the computer 22. The details of the signal measurement stage S30a will be explained with reference to FIG. 11. The details of the signal correction stage S30b will be explained with reference to FIG. 12.

Figure 10:
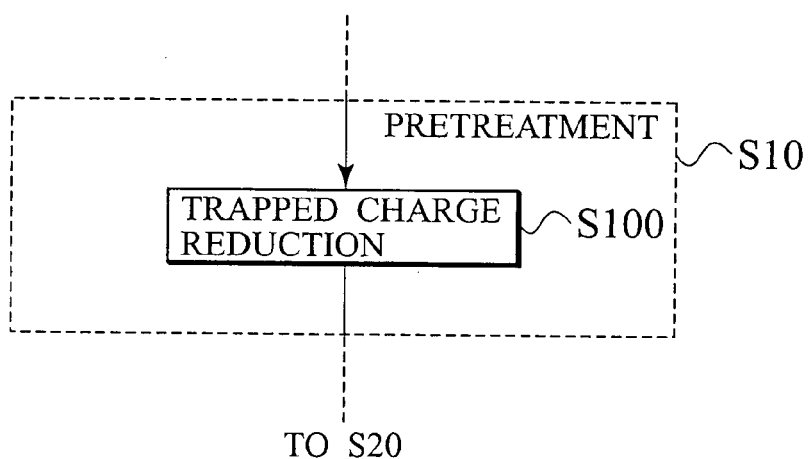
FIG. 10 is a flowchart showing the details of a pretreatment stage (S10) of FIG. 9.

As shown in FIG. 10, the pretreatment stage S10 of FIG. 9 includes stage S100 that reduces charge trapped in the topmost surface of the wafer 1. The trapped charge involves chemical oxide. The trapped charge reducing stage (S100) may include a wet process that applies a dilute hydrofluoric acid solution to the surface of the wafer 1 or a termination process that terminates crystal defects in the wafer 1 with hydrogen (H) atoms. The wet process exposes the surface of the wafer 1 to a dilute hydrofluoric acid solution and removes a topmost film containing much trapped charge from the wafer 1. The termination process leaves the wafer 1 in a hydrogen atmosphere at a high temperature, to allow hydrogen atoms terminate crystal defects in a region of the wafer 1 where ions are implanted.

(Signal Measurement)

Figure 11:
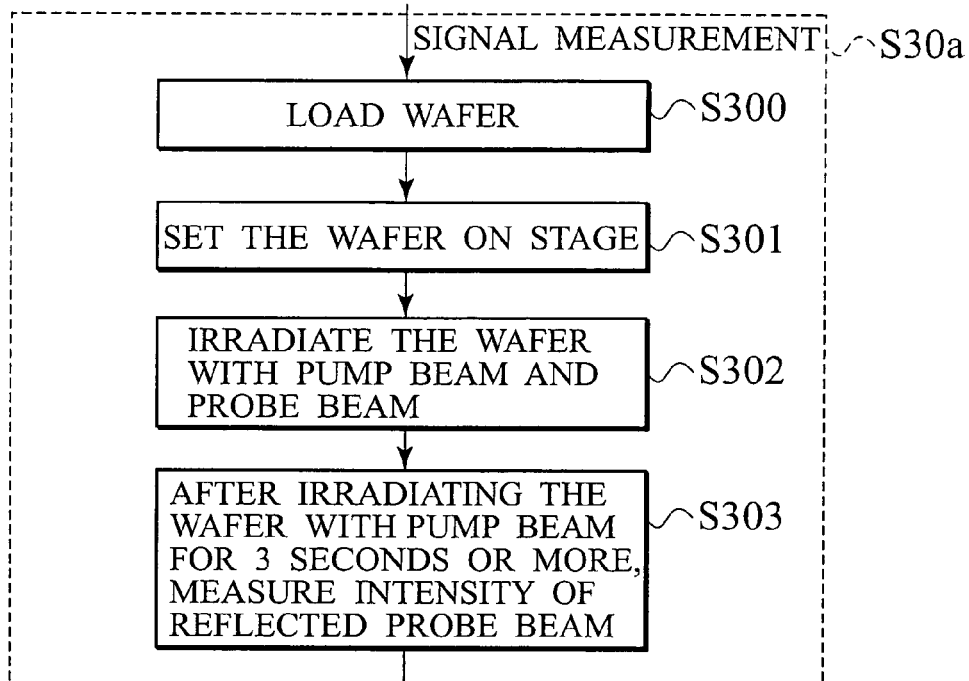
FIG. 11 is a flowchart showing the details of a signal measurement stage (S30a) of FIG. 9.

As shown in FIG. 11, the signal measurement stage S30a of FIG. 9 includes stages S300 to S303.

(A) Stage S300 loads the wafer 1 into the chamber 18 of FIG. 2 through the load port 19.

(B) Stage S301 sets the wafer 1 on the stage 10.

(C) Stage S302 drives the pump laser 11 and probe laser 12 to emit a pump beam 25 and probe beam 26 toward a target area on the surface of the wafer 1.

(D) Stage S303 irradiates the wafer 1 with the pump beam 25 for at least 3 seconds, and while irradiating the pump beam 25 and probe beam 26 on the surface of the wafer 1, measures the intensity of a reflected probe beam 28 using the detector 13 and lock-in amplifier 21.

(Signal Correction)

Figure 12:
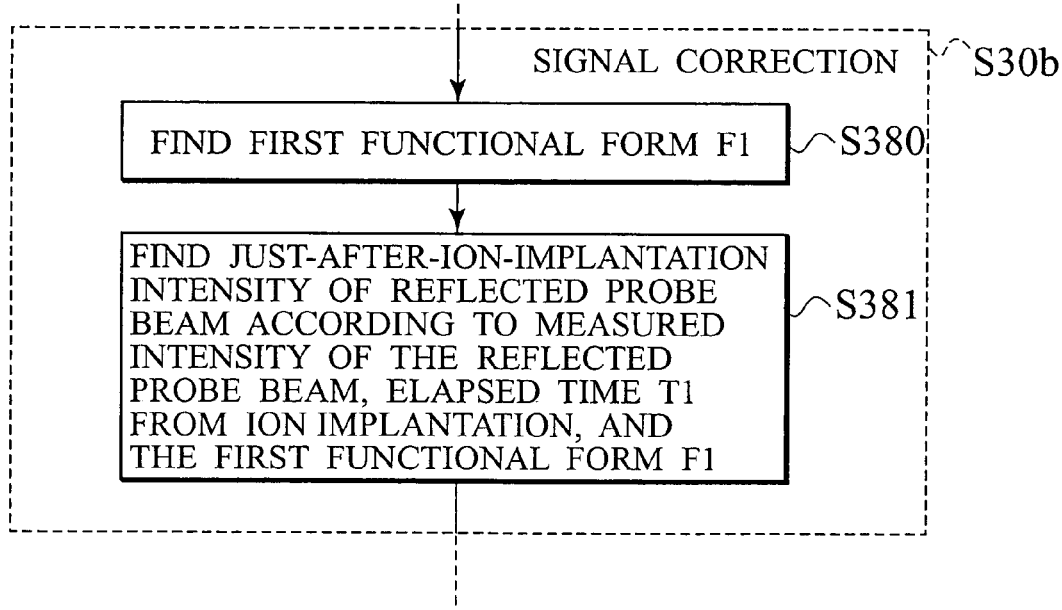
FIG. 12 is a flowchart showing the details of a signal correction stage (S30b) of FIG. 9.
Figure 13:
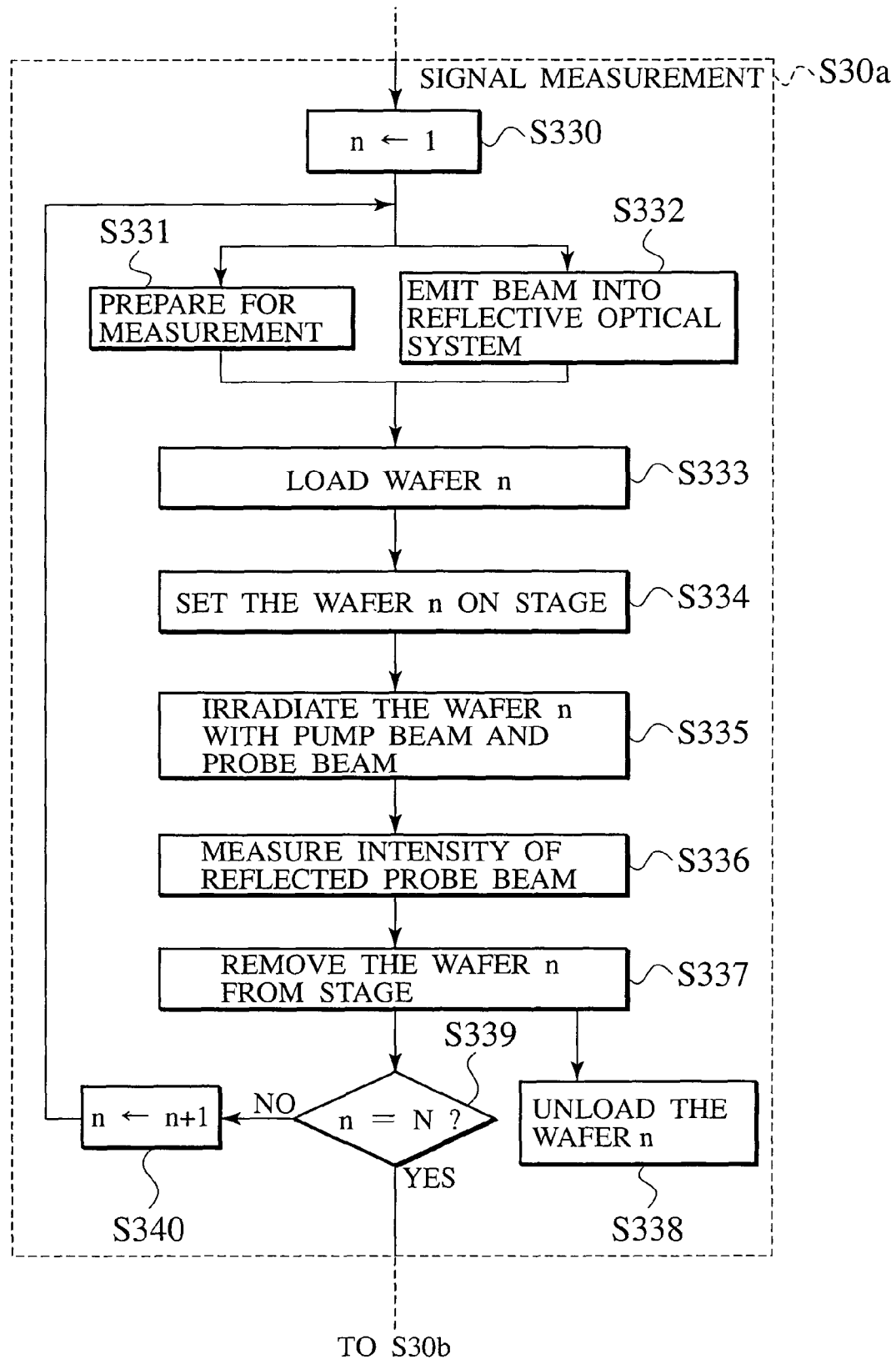
FIG. 13 is a flowchart showing the details of a first modification of the signal measurement stage (S30a)

As shown in FIG. 12, the signal correction stage S30b of FIG. 9 includes stages S380 and S381.

Figure 8:
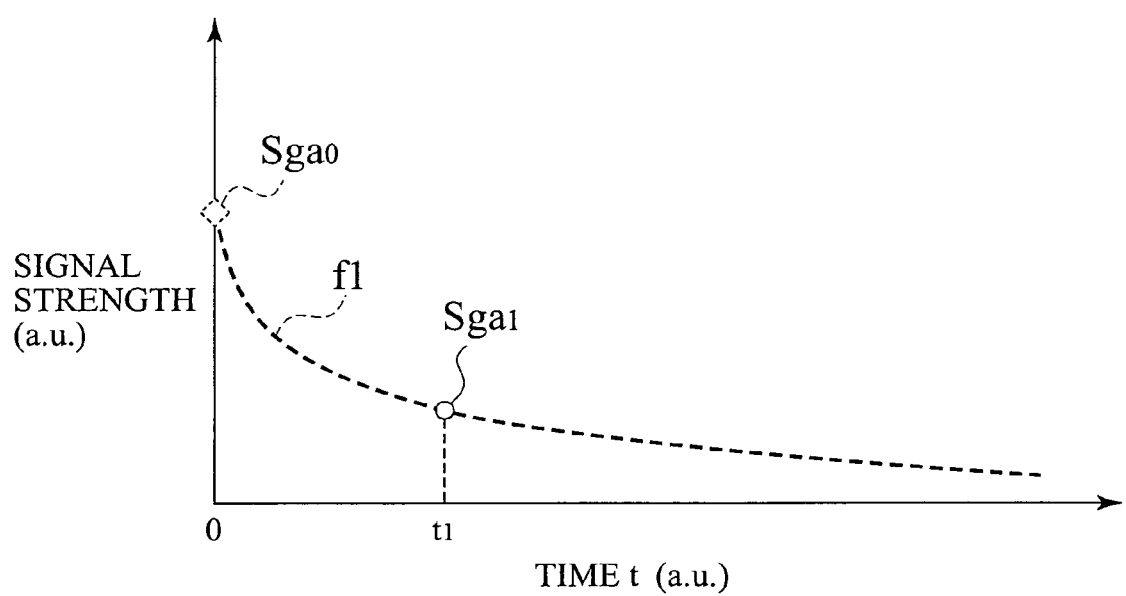
FIG. 8 is a graph showing an example of a first functional form f1 stored in a first functional form database in the computer of FIG. 7.

(a) Stage S380 beforehand finds first functional forms such as the first functional form f1 of FIG. 8. More precisely, the apparatus of FIG. 2 is employed to measure signals after different time periods elapsed from ion implantation. For the measured signal values, the first functional form f1 of the expression (5) is fitted to find the correction coefficients of the expression (5). The first functional forms with the found coefficients are stored in the first functional form database 61.

(b) Stage S381 finds a signal strength Sga0 of just after ion implantation according to a signal strength Sga1 of FIG. 8, time interval elapsed from the time of the ion implantation to time t1, and the first functional form f1.

The pretreatment stage S100 of FIG. 10 can reduce charge trapped in the wafer 1, so that the inspection stage S30 of FIG. 9 may properly be carried out. Unlike the related art that involves trapped charge in the topmost surface of a wafer causing measurement errors of several tens of percents, the embodiment of the present invention reduces the trapped charge to correctly measure the intensity and phase of the reflected probe beam 28 and accurately read a crystallographic state in the wafer 1. In addition, the embodiment of the present invention eliminates a process of removing a topmost layer of the wafer 1 after the ion implantation stage S20 and before the inspection stage S30. Even if semiconductor devices on the wafer 1 involve a shallow pn junction, the embodiment of the present invention causes no damage to the characteristics of the semiconductor devices. The trapped charge reducing stage S100 of FIG. 10 minimizes the influence of trapped charge on the measurement of the reflected probe beam 28 and on a recombination of photocarriers pumped in the wafer 1. For example, stage S100 can prevent absorption of the pump beam 25, probe beam 26, and reflected probe beam 28 by the trapped charge in the wafer 1. Conducting the trapped charge reducing stage S100 before the ion implantation stage S20 makes it possible to read ion implantation information. Such information would be lost if the trapped charge reducing stage S100 was carried out after the ion implantation stage S20. Without losing information about the topmost layer of the wafer 1 and without being influenced by trapped charge, the embodiment of the present invention can accurately evaluate the characteristics of the wafer 1.

The apparatus of FIG. 2 can detect not only the dose and profile of implanted ions but also microdefects in the wafer 1. It is known that a distribution of microdefects in a wafer changes even at a room temperature. Accordingly, even if an in-plane uniformity of implanted ions is controlled at 1% over a wafer, a signal strength will increase by several percents when microdefects in the wafer greatly vary.

The ion implantation stage S20 properly selects an ion implanting angle according to ion implanting conditions, so that, when ions are implanted in each wafer on the wheel 4 that is turned, microdefects may uniformly be distributed over the wafer 1. Therefore, in-plane signal variations caused by microdefects in the wafer decrease and the semiconductor material is accurately evaluated. The ion implanting angle may be selected so as to reduce the influence of channeling on ion implantation and minimize signal variations over the wafer 1. When implanting phosphorus (P) ions in the wafer 1 at an acceleration energy of 500 keV, the angle between the rotation axis 5 of the wheel 4 and the ion beam 2 may be within ±2.5 degrees around a parallel level, to keep an in-plane uniformity of signal strengths on the wafer 1 within 1% on ion dose basis.

Employing a relatively large ion implanting acceleration energy intensifies an ion implantation channeling phenomenon and interaction between implanted ions and interstitial-atoms, thereby deteriorating an in-plane uniformity of signal strengths. Employing a relatively small ion implanting acceleration energy realizes a high in-plane uniformity of signal strengths. The employment of the ion implanting method of the embodiment of the present invention is effective in improving the in-plane uniformity of signal strengths even with a relatively high ion implanting acceleration energy.

The signal measurement stage S30a irradiates the wafer 1 with the pump beam 25 for at least three seconds before signal measurement. Therefore, a thermodynamic metastable state for the behaviors of point defects generated by ion implantation is formed, in order to stabilize the generation and annihilation reactions of vacancies and interstitial-atoms in the wafer 1. Since signals are measured at thermal equilibrium, a life time (τ) to recombination of excess carriers and the signals are stabilized. Assuming the pump laser 11 has a laser power of 80 mW and a modulation frequency of 2 kHz applied to the pump beam 25, a wait time before signal measurement may be extended from 0.3 seconds to 3 seconds, to improve a standard deviation indicative of the reproducibility of measured signals to ⅕.

The signal correction stage S30b can compute a signal strength of the reflected probe beam 28 just after ion implantation without regard to elapsed time from ion implantation to signal measurement.

(First Modification of Signal Measurement)

By referencing to FIGS. 13 and 14A to 14D, a first modification of the signal measurement stage S30a of FIG. 9 will be explained. The first modification continuously measures N pieces of wafer in stages S330 to S340.

(a) Stage S330 sets n=1 to select a wafer n as a first wafer to measure, where "n" is a natural number in 1 to N.

(b) Stage S331 prepares for measuring the first wafer (n=1). Namely, stage S331 adjusts the optical system for irradiating a pump beam 25 and probe beam 26 and the optical system for providing a reflected pump beam 27 and reflected probe beam 28.

Figure 14A:
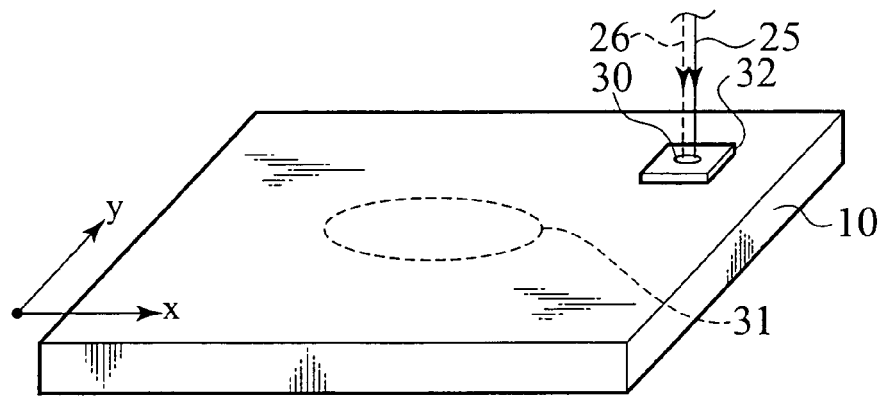
FIGS. 14A to 14D are perspective views showing areas irradiated with a pump beam and probe beam on the stage according to the modification of FIG. 13.

(c) In parallel with stage S331, stage S332 generates a beam equivalent to the reflected probe beam 28 of FIG. 2 along an optical path equivalent to that of the reflected probe beam 28. More precisely, a reflector, having the same reflectance as the surface of the first wafer, is arranged in an optical path of the probe beam 26 and is irradiated with the probe beam 26. As shown in FIG. 14A, a dummy sample 32 serves as the reflector placed on the stage 10. The stage 10 is moved in x and y directions to set an irradiation area 30 on the dummy sample 32. The position of the dummy sample 32 on the stage 10 is different from a wafer position 31 on the stage 10 where the first wafer is placed.

Figure 14B:
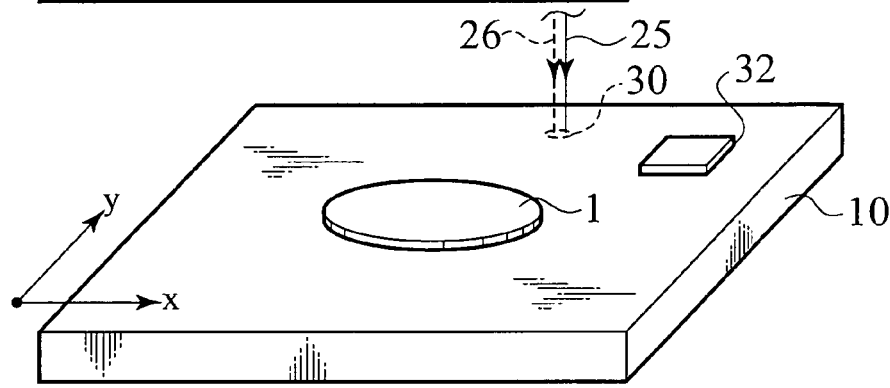

(d) After stage S331, stage S333 loads the first wafer into the chamber 18. Stage S334 sets the first wafer to the wafer position 31 on the stage 10 as shown in FIG. 14B. At this time, the irradiation area 30 may be out of the dummy sample 32 and first wafer.

Figure 14C:
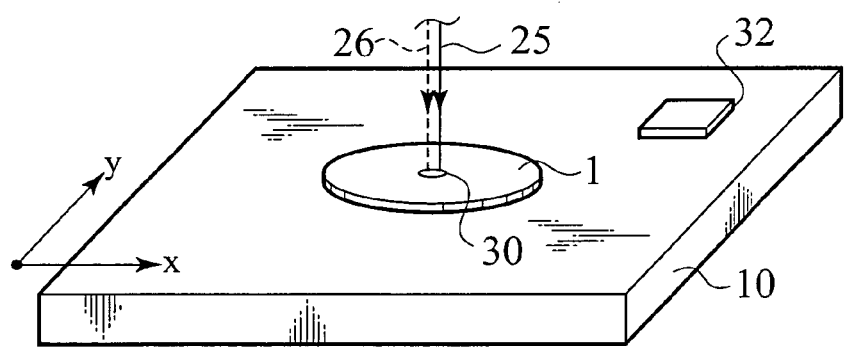

(e) Stage S335 irradiates a required area on the surface of the first wafer with the pump beam 25 and probe beam 26 as shown in FIG. 14C.

(f) While irradiating the surface of the first wafer with the pump beam 25 and probe beam 26, stage S336 measures the intensity of a reflected probe beam 28 with the detector 13 and lock-in amplifier 21.

Figure 14D:
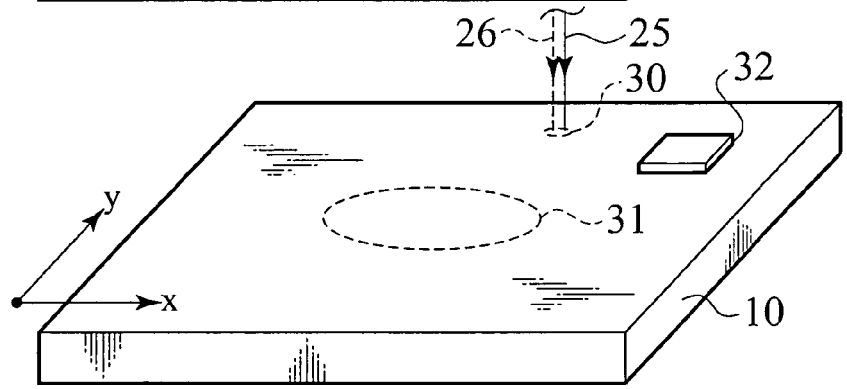

(g) Stage S337 removes the first wafer from the stage 10 as shown in FIG. 14D. Stage S338 takes the first wafer out of the chamber 18 through the load port 19.

(h) Stage S339 determines whether or not n=N. This is the first cycle with stage S330 setting n=1, and therefore, stage S339 is "NO" and stage S340 adds 1 to n to make n=2. The flow returns to stages S331 and S332 to repeat stages S331 through S337 on the second wafer. In this way, the loop of stages S331 to S339 is repeated on the wafers 1 to N.

Even during a no-measurement period of irradiating no probe beam 26 on a wafer, the first modification emits the pump beam 25 and probe beam 26 for the reflection optical system. Even if the reflection optical system involves thermal expansion or even if the sensitivity of the detector 13 varies between a light receiving period and a no-light receiving period, the first modification causes no shift in the reflection optical system. This results in temporally stabilizing signal measurement and improving the reproducibility of measurement. For example, a plurality of signal measurements may continuously be carried out according to the modification after a standby time of one hour or more. Even in this case, the first modification causes no measurement errors between the first measurement and the subsequent measurements. Without regard to the operating or standby conditions of the semiconductor material evaluation apparatus, the first modification can stably measure signals. The reflection optical system includes the objective lens 17, second half-mirror 15, and filter 16 arranged in the optical path of the reflected probe beam 28 between the wafer n and the detector 13. The dummy sample 32 has a similar crystal structure to that of the wafer n and receives a similar surface treatment to that for the wafer n.

When it is difficult to place the dummy sample 32 on the stage 10, a mirror to reflect an incident beam may be interposed in the optical system of the apparatus of FIG. 2. Alternatively, a mirror and an optical wavefront regenerator may be employed to guide a beam to the reflection optical system. It is preferable to start stage S332 within three minutes after measuring a reflected probe beam from a wafer n in stage S336 and continue stage S332 to a time point within three minutes before the irradiation of the probe beam 26 on a wafer n+1 in stage S335. Stage S332 may irradiate not only the probe beam 26 but also the pump beam 25 on the dummy sample 32, so that the same beams as those for signal measurement may enter the reflection optical system during the measurement preparation stage S331. The first modification of signal measurement is applicable not only to the first semiconductor material evaluation method but also to the second semiconductor material evaluation method mentioned above.

(Second Modification of Signal Measurement)

By referencing to FIGS. 15 and 16, a second modification of the signal measurement stage S30a of FIG. 9 will be explained.

Figure 15:
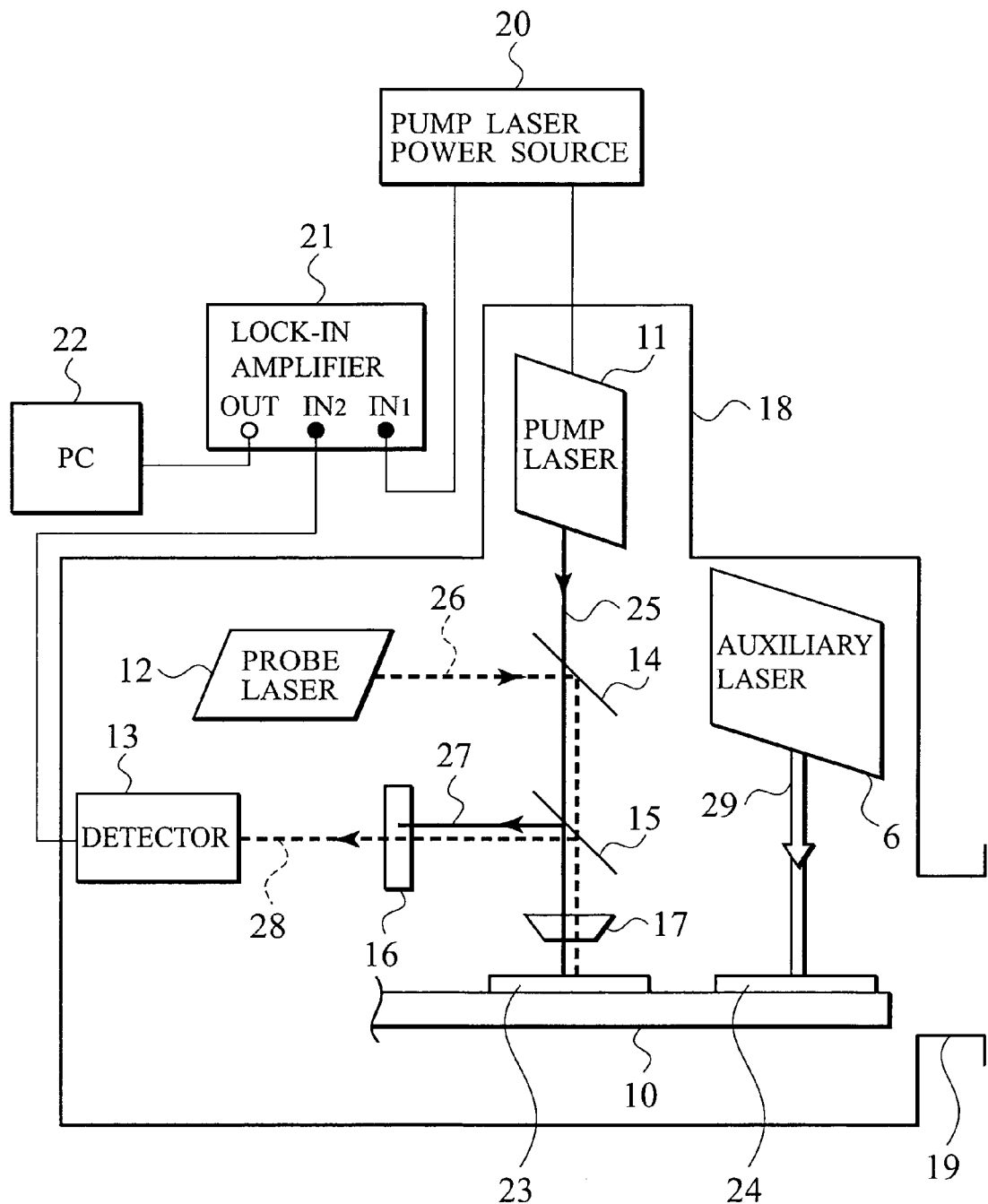
FIG. 15 is a block diagram showing an apparatus for evaluating semiconductor material employed by a second modification of the signal measurement stage (S30a)
Figure 16:
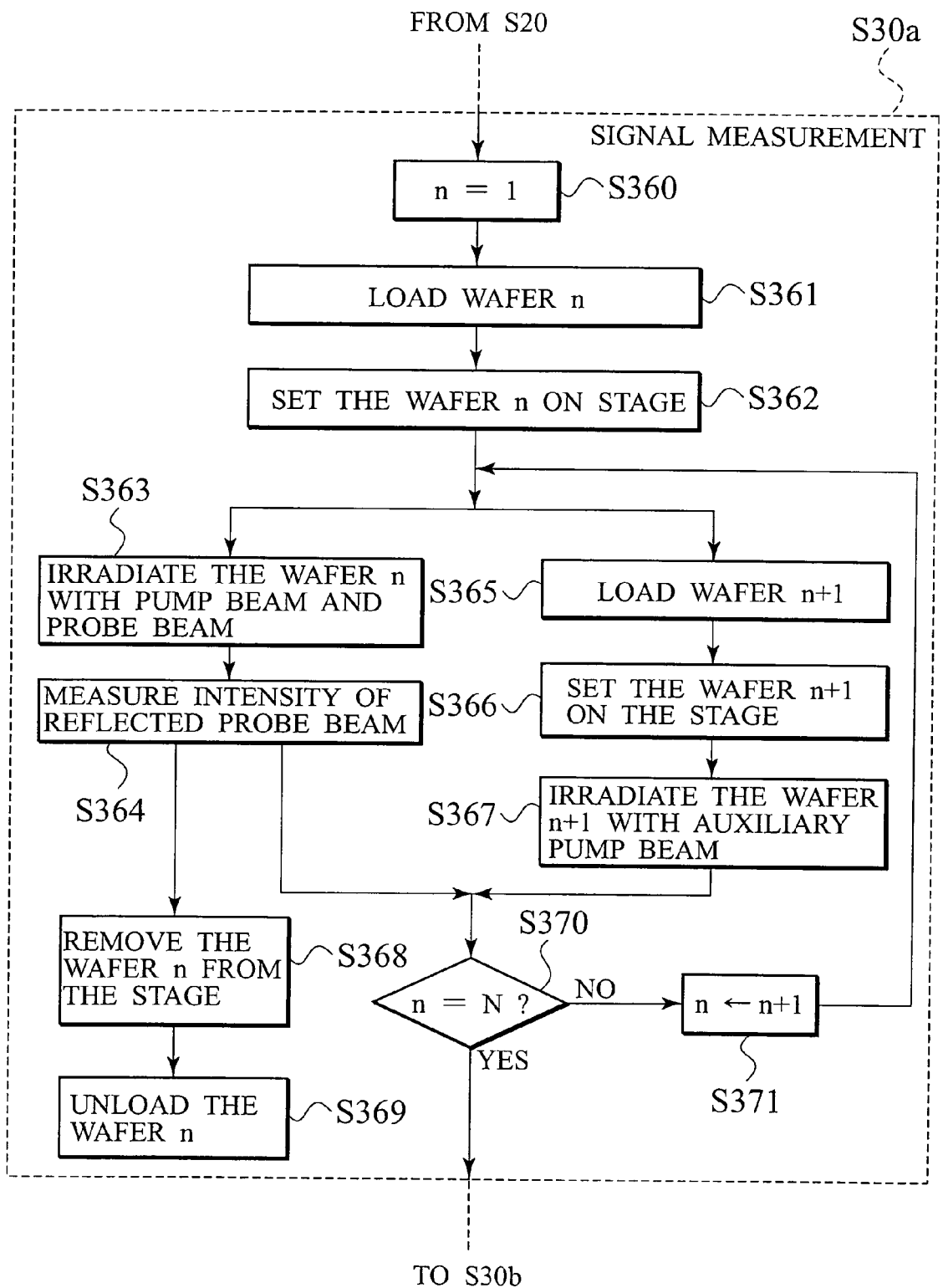
FIG. 16 is a flowchart showing the details of the second modification of the signal measurement stage (S30a)

FIG. 15 shows an apparatus for evaluating semiconductor material employed for the second modification. A pump laser 11 irradiates a pump beam 25 on a first wafer 23. A probe laser 12 irradiates a probe beam 26 on the first wafer 23. A detector 13 detects a reflected probe beam 28. An auxiliary laser 6 irradiates an auxiliary pump beam 29 on a second wafer 24 that is different from the first wafer 23. The auxiliary pump beam 29 has photon energy to pump photocarriers in the second wafer 24. The apparatus of FIG. 15 further includes the first and second half-mirrors 14 and 15, filter 16, objective lens 17, chamber 18, load port 19, pump laser power source 20, lock-in amplifier 21, and computer 22.

The first and second wafers 23 and 24 are arranged on the same stage 10. During signal measurement on the first wafer 23, the auxiliary laser 6 irradiates the auxiliary pump beam 29 on the second wafer 24. After the signal measurement on the first wafer 23, the stage 10 is moved to carry out signal measurement on the second wafer 24. Namely, just before starting signal measurement on the second wafer 24, the auxiliary pump beam 29 irradiates the second wafer 24 for at least three seconds. The thermodynamic metastable state is established in the second wafer 24 in coordination with the behaviors of point defects caused by ion implantation, to stabilize the generation and annihilation reactions of vacancies and interstitial-atoms in the second wafer 24. Measuring signals under such a thermodynamic metastable state stabilizes a life time ($\tau$) to recombination of excess carriers as well as the signals themselves. Just after the completion of the signal measurement on the first wafer 23, signal measurement on the second wafer 24 can be started. A plurality of wafers can be processed continuously with great efficiency.

By referencing to FIG. 16, the signal measurement stage (S30a) employing the apparatus of FIG. 15 will be explained. The signal measurement stage of FIG. 16 continuously measures N pieces of wafer in stages S360 to S371.

(A) Stage S360 sets n=1 to select a wafer n as the first wafer 23 in FIG. 15, where "n" is a natural number in 1 to N.

(B) Stage S361 loads the first wafer 23 into the chamber 18 through the load port 19. Stage S362 sets the first wafer 23 on the stage 10.

(C) Stage S363 irradiates a required area on the surface of the first wafer 23 with a pump beam 25 and probe beam 26. While irradiating the pump beam 25 and probe beam 26 on the first wafer 23, stage S364 measures the intensity of a reflected probe beam 28 using the detector 13 and lock-in amplifier 21.

(D) In parallel with stages S363 and S364, stages S365 to S367 are carried out. Stage S365 loads a wafer n+1 as the second wafer 24 in FIG. 15 into the chamber 18 through the load port 19. Stage S366 sets the second wafer 24 on the stage 10. Stage S367 irradiates a required area on the surface of the second wafer 24 with an auxiliary pump beam 29.

(E) After the completion of stage S364, stage S370 checks to see if n=N. This is the first cycle with stage S360 setting n=1, and therefore, stage S370 is "NO" and stage S371 adds 1 to n to make n=2. The flow returns to stage S363 to carry out stages S363 and S364 on the second wafer 24. At the same time, stages S365 to S367 are carried out on a third wafer in parallel with the processing of the second wafer 24. In this way, the loop of stages S363 to S367 is repeated on the wafers 1 to N.

(F) After the completion of stage S364, stage S368 removes the wafer n from the stage 10, and stage S369 takes the wafer n out of the chamber 18 through the load port 19.

The second modification measures signals on a wafer n, and at the same time, irradiates a wafer n+1 with the auxiliary pump beam 29 from the auxiliary laser 6. The second modification measures signals on the wafer n+1 just after the completion of signal measurement on the wafer n. A plurality of wafers are continuously processed with efficiency. It is possible to irradiate the wafer n+1 with the auxiliary pump beam 29 for at least three seconds just before starting signal measurement on the wafer n+1. A thermodynamic metastable state is established before starting signal measurement on the wafer n+1 in connection with the behaviors of point defects caused by ion implantation, to stabilize the generation and annihilation reactions of vacancies and interstitial-atoms in the wafer n+1.

(Modification of Pretreatment)

Figure 17:
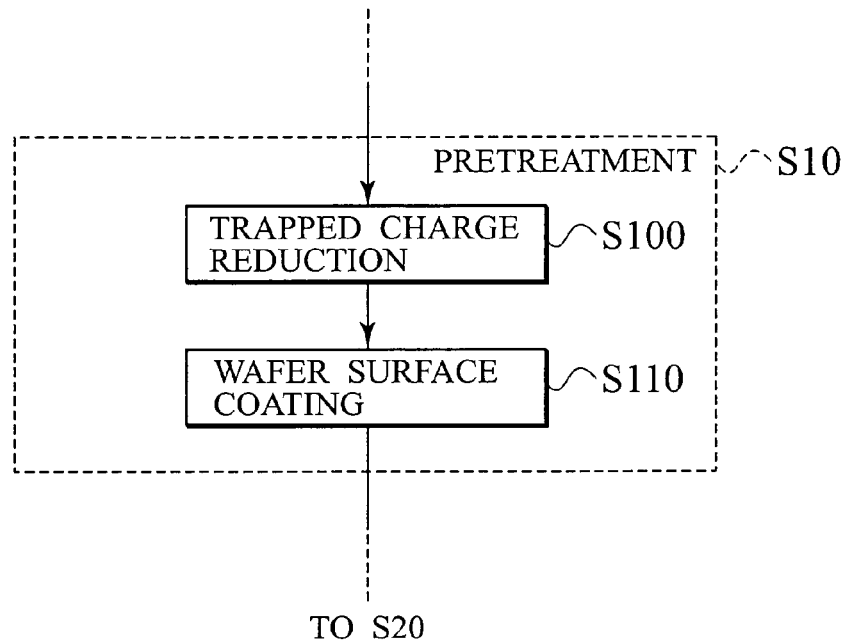
FIG. 17 is a flowchart showing a modification of the pretreatment stage (S10) of FIG. 9.

By referencing to FIG. 17, a modification of the pretreatment stage S10 of FIG. 9 will be explained. The modification of the pretreatment stage S10 includes stages S100 and S110.

(a) Stage S100 reduces charge trapped in the topmost surface of a wafer 1. The trapped charge involves chemical oxide. The trapped charge reducing stage S100 involves, for example, a wet process that applies a dilute hydrofluoric acid solution to the surface of the wafer 1 or a termination process of terminating crystal defects in the wafer 1 with hydrogen (H) atoms. More precisely, the wet process exposes the surface of the wafer 1 to a dilute hydrofluoric acid solution to remove a topmost film containing much trapped charge from the wafer 1. The termination process leaves the wafer 1 in a hydrogen atmosphere at a high temperature to allow hydrogen atoms to terminate crystal defects in the surface of the wafer 1 and in a region of the wafer 1 where ions are implanted. Stage S100 of FIG. 17 is the same as stage S100 of FIG. 10.

(b) Stage S110 coats the surface of the wafer 1 with an insulating film. The insulating film may be a thermal oxide formed on the top surface of the wafer 1 by heat treatment, or an oxide film, a nitride film, or an oxynitride film deposited on the surface of the wafer 1 by, for example, chemical vapor deposition (CVD).

The pretreatment before ion implantation according to the modification of the pretreatment stage provides the same effectiveness as the pretreatment stage S10 of FIG. 10. In addition, stage S110 of the modification protects the surface of the wafer 1 with an insulating film and keeps the surface of the wafer 1 in a trapped charge minimized state for a long time.

(Modification of Signal Correction)

By referencing to FIGS. 18 to 20, a modification of the signal correction stage S30b of FIG. 9 will be explained.

Figure 18:
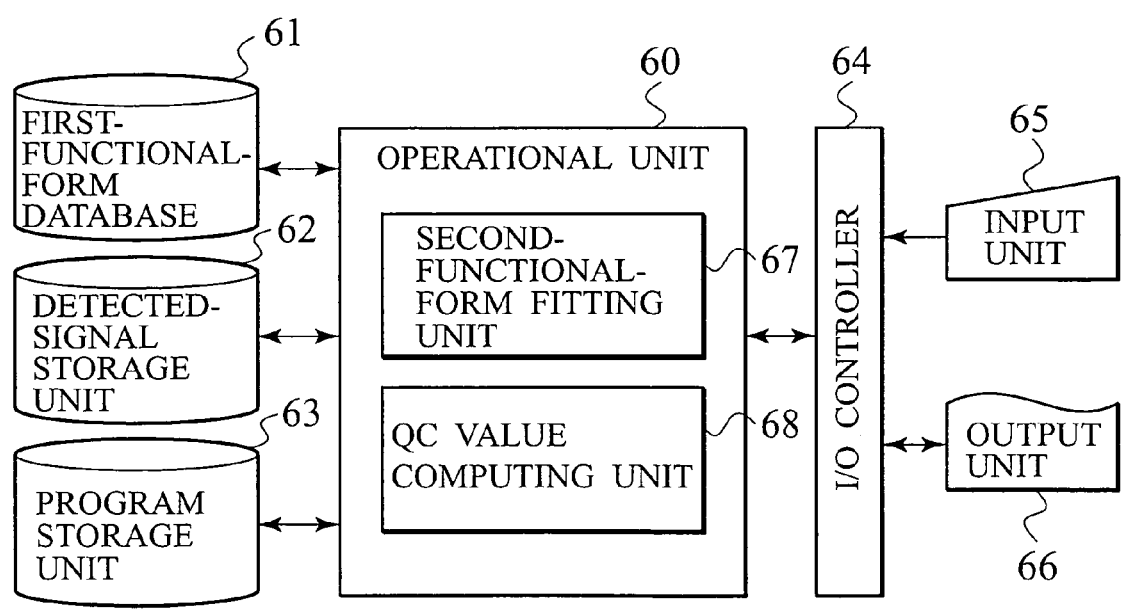
FIG. 18 is a block diagram showing a computer employed by a modification of the signal correction stage (S30b) of FIG. 9.

The modification of the signal correction employs a computer 22 shown in FIG. 18. The computer has an operational unit 60 having a function of correcting the strength of a signal supplied from the lock-in amplifier 21 of FIG. 2, a first functional form database 61 connected to the operational unit 60, a detected signal storage unit 62 connected to the operational unit 60, a program storage unit 63 connected to the operational unit 60, an I/O controller 64, an input unit 65, and an output unit 66. The operational unit 60 has a second functional form fitting unit 67 and a QC value computing unit 68.

The second functional form fitting unit 67 finds a second functional form f2 according to strengths of a reflected probe beam 28 stored in the detected signal storage unit 62 and elapsed time from the start of irradiation of a probe beam 26 to measurement time points of intensities of the reflected probe beam 28 stored in the detected signal storage unit 62. The second functional form f2 indicates intensity changes of the reflected probe beam 28 relative to elapsed time after the start of irradiation of the probe beam 26. The details of the second functional form f2 will be explained with reference to FIG. 19.

The QC value computing unit 68 utilizes an estimated intensity of the reflected probe beam 28 just after irradiation of the probe beam was begun, elapsed time from ion implantation to a measurement time point of the intensity of the reflected probe beam 28, and a first functional form f1, to find an intensity of the reflected probe beam 28 just after ion implantation.

Figure 19:
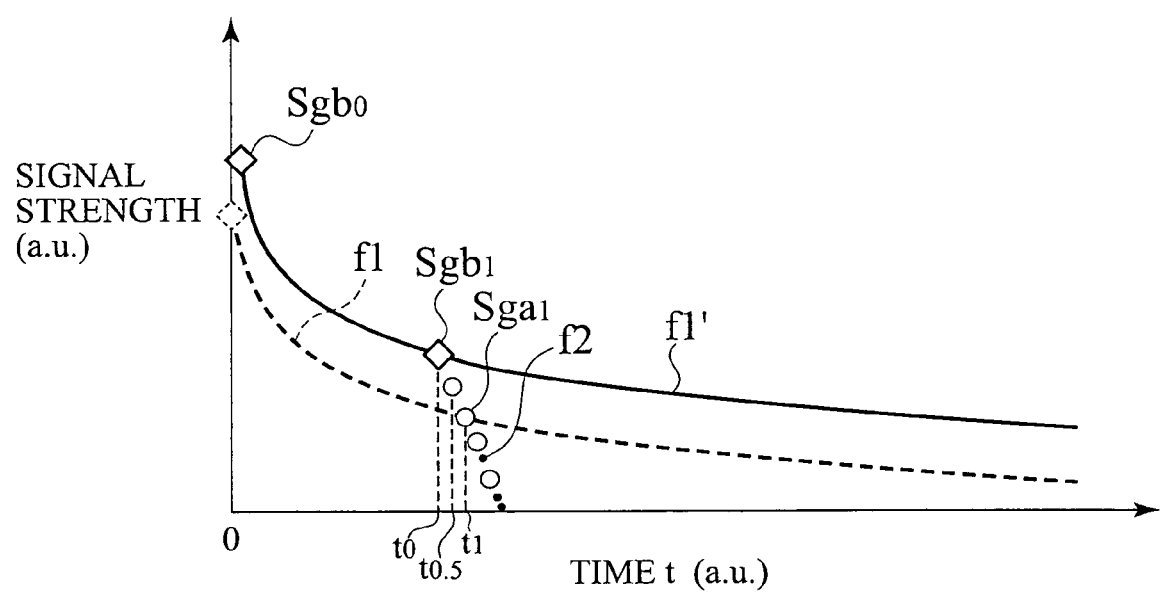
FIG. 19 is a graph showing an example of a first functional form f1 stored in a first functional form database of FIG. 18, an example of a newly prepared first functional form f1', and an example of a second functional form f2 provided by a second functional form fitting unit of FIG. 18.
Figure 20:
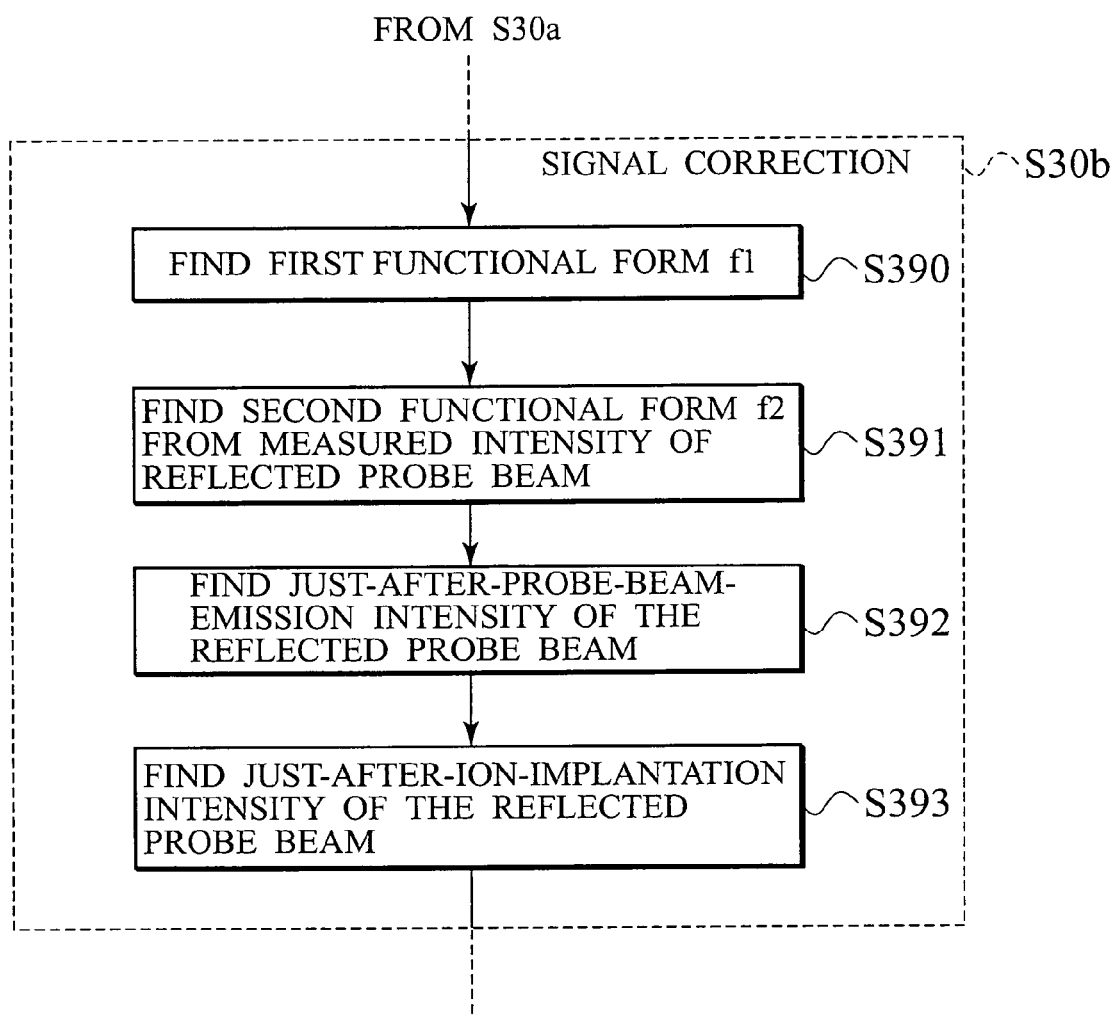
FIG. 20 is a flowchart showing the details of the modification of the signal correction stage (S30b) employing the computer of FIG. 18.

In FIG. 19, a typical profile of a second functional form f2 provided by the second functional form fitting unit 67 is shown. An abscissa indicates elapsed time from ion implantation, and an ordinate indicates signal strength. The profile of the second functional form f2 is formed by fitting a plurality of circles representing measured signal strengths including a signal strength Sga1. The signals are measured at t0.5, t1, and the like after t0 when the irradiation of the probe beam 26 is begun. As indicated with a first functional form f1 in FIG. 19, signal strengths decrease according to elapsed time from ion implantation. In addition, as indicated regarding the second functional form f2, signal strengths more decrease sharply than the first functional form f1 after the irradiation of the probe beam 26 was begun.

The signal strength Sga1 is measured after a period between t0 and t1 the irradiation of the probe beam 26. The first functional form f1 shows a relationship between a signal strength measured a given period after the irradiation of the probe beam 26 was begun and elapsed time from ion implantation. There must be a new first functional form f1' that indicates a relationship between a signal strength just after the irradiation of the probe beam 26 was begun and elapsed time from ion implantation. The new first functional form f1' and the first functional form f1 have different signal strengths just after ion implantation. It is necessary to find a signal strength Sgb0 just after ion implantation and just after the irradiation of the probe beam 26 was begun. This is because, as the second functional form f2 shows, signal strengths more decrease suddenly than the first functional form f1 depending on the elapsed time from the irradiation of the probe beam 26. The first functional form f1 and new first functional form f1' are stored in the first functional form database 61.

The second functional form f2 is expressed as follows by adding up a plurality of terms including logarithms of elapsed time after the start of irradiation of the probe beam 26:

$$f2 = A0 + D_1 \exp\{-(t-t_0)/\tau v_1\} + D_2 \exp\{-(t-t_0)/\tau v_2\} + \Sigma D_k \exp\{-(t-t_0)/\tau v_k\} \quad (6)$$

where A0, $D_1$, $D_2$, $D_k$, $\tau v_1$, $\tau v_2$, and $\tau v_k$ are correction coefficients and $t_0$ is time to begin the irradiation of the probe beam 26. The apparatus of FIG. 2 is employed to measure signals at different elapsed time periods after the irradiation of the probe beam 26 was begun and find the correction coefficients. The correction coefficients of the second functional form f2 vary according to ion implanting conditions and irradiation periods of the probe beam 26. Generally, the second functional form f2 is sufficiently expressible with the first to third terms of the right side of the expression (6), and the fourth term thereof may be added if required.

By referencing to FIG. 20, a modification of the signal correction stage S30b of FIG. 9 employing the computer of FIG. 18 will be explained. The modification consists of stages S390 to S393.

(a) Stage S390 finds a new first functional form f1' of FIG. 19. More precisely, the apparatus of FIG. 2 is employed to measure signals at different elapsed time periods after ion implantation. To the measured signal values, the first functional form f1 of the expression (5) is fitted to find the correction coefficients of the expression (5). The found correction coefficients are stored in the first functional form database 61. From among the first functional forms stored in the database 61, an optimum one is selected according to the measured signal values.

(b) Stage S391 employs the second functional form fitting unit 67 to find a second functional form f2 according to an intensity of the reflected probe beam 28 and elapsed time from the irradiation of the probe beam 26 and a measurement time point of the intensity of the reflected probe beam 28. More precisely, signals are actually measured at t0.5, t1, and the like after time t0 when the irradiation of the probe beam 26 is begun. To the measured signal values, the second functional form f2 of the expression (6) is fitted to find the correction coefficients of the expression (6). For example, the second functional form f2 is fitted to the measured strengths depicted with the circles in FIG. 19 including the measured strength Sga1.

(c) Stage S392 employs the QC value computing unit 68 to find an intensity of the reflected probe beam 28 just after the irradiation of the probe beam 26 was begun according to the second functional form f2. For example in FIG. 19, a signal strength Sgb1 at t0 is calculated according to the second functional form f2.

(d) Stage S393 employs the QC value computing unit 68 to find an intensity of the reflected probe beam 28 just after ion implantation according to the intensity of the reflected probe beam 26 just after the beginning of irradiation thereof, elapsed time from ion implantation to the measurement time point of-the intensity of the reflected probe beam 28, and the new first functional form f1'. For example in FIG. 19, the signal strength Sgb1 at t0 and the new first functional form f1' are used to find a signal strength Sgb0 just after ion implantation and just after the beginning of irradiation of the probe beam 26.

As mentioned above, a temporal change in signal strength includes a component that depends on the time elapsed from the completion of ion implantation and a component that depends on a signal measuring period, i.e., a period for irradiating the probe beam 26. The signal correction stage (S30b) mentioned above can compute a signal strength corresponding to the reflected probe beam 28 just after ion implantation without regard to the time elapsed from ion implantation to a signal measurement time point. Even by signal measurement made after a given period from the beginning of irradiation of the probe beam 26, the modification of FIG. 20 can find the signal strength Sgb0 just after ion implantation and just after the beginning of irradiation of the probe beam 26. The modification may measure signals after irradiating the pump beam 25 for three seconds or longer in stage S303 of FIG. 11, and according to the measured signals, the modification can more accurately calculate an initial signal strength than the signal correction stages S380 and S381 of FIG. 12. The modification, therefore, is capable of speedily and correctly finding the various characteristics of semiconductor material at the beginning of irradiation of the probe beam 26. The modification can correct signal strength changes caused by deterioration of the performance of, for example, the probe laser 12, thereby improving the reliability of measured values.

In particular, the modification can accurately evaluate the characteristics of semiconductor material when there are temporal changes in measured signal values due to changes in vacancy concentrations and vacancy cluster concentrations in the semiconductor material.

FIRST EXAMPLE OF ION IMPLANTATION

A first example of the ion implantation stage S20 of FIG. 9 with the ion beam 2 of FIG. 1 having a given acceleration energy will be explained. The first example employs a relatively high acceleration energy for the ion beam 2.

The ion implanter of FIG. 1 utilizes an axis of the ion beam 2 and the rotation axis 5 of the wheel 4, to determine an ion implantation angle relative to the surface of a wafer 1. The ion implanter of FIG. 1 is a batch-type ion implanter that turns the wheel 4 to uniformly implant ions in a plurality of wafers arranged on the wheel 4.

In stage S20, the ion implanter of FIG. 1 implants phosphorus (P) ions in wafers at an acceleration energy of 500 keV. In stage S30a after the ion implantation, the semiconductor material evaluation apparatus of FIG. 2 measures a reflected probe beam 28. When the ion beam 2 is substantially in parallel with the rotation axis 5 of the wheel 4, variations in measured signal strengths are small over the surface of the wafer 1 during the signal measurement stage S30a, thus minimizing measurement variations over the surface of the wafer 1. Therefore, positional variations in measurements on the wafer 1 decrease and measurement reproducibility is improved.

In FIG. 21, various angles between the ion beam 2 and the rotation axis 5 of the wheel 4 and corresponding values indicative of in-plane uniformity of signal strengths are shown. When the angle of the ion beam 2 relative to the rotation axis 5 of the wheel 4 is +2 degrees, parallel (0 degrees), or −2 degrees, a standard deviation on dose basis of signal strengths over the surface of the wafer 1 is low to suppress in-plane variations. When the angle is −5 degrees, the standard deviation is large to increase in-plane variations. Consequently, when the ion beam 2 is in parallel with the rotation axis 5 of the wheel 4, or forms an angle of +2.5 degrees or less relative to the rotation axis 5, in-plane variations of signal strengths on the wafer 1 are suppressed. According to the first example, an oxide film of about 8 nm thick is formed on the surface of the wafer 1 before ion implantation.

An acceleration energy for high-acceleration ion implantation depends on ionic species. Although the first example employs phosphorus (P) ions, other ionic species are also employable. Irrespective of whether or not an oxide film of about 10 nm thick is formed on the surface of a wafer in ion implantation, a proper in-plane uniformity of signal strengths will be achieved when the ion beam 2 is substantially in parallel with the rotation axis 5 of the wheel 4.

In the ion implantation stage S20, an angle between the ion beam 2 and the wafer 1 may be set to minimize a deviation of the angle. In-plane intensity variations of the reflected probe beam 28 on the wafer 1 are suppressed and proper reproducibility of measurement is realized.

SECOND EXAMPLE OF ION IMPLANTATION

A second example of the ion implantation stage S20 of FIG. 9 employs a relatively low acceleration energy for the ion beam 2.

In stage S20, the ion implanter of FIG. 1 implants boron (B) ions in a wafer 1 at an acceleration energy of 3 keV. Before the ion implantation, a natural oxide film formed on the surface of the wafer 1 is removed with dilute hydrofluoric acid. In stage S30a after the ion implantation, the apparatus of FIG. 2 measures a reflected probe beam 28 from the wafer 1. At this time, when the ion beam 2 is substantially in parallel with the rotation axis 5 of the wheel 4, in-plane variations in signal strengths on the wafer 1 will be small.

When ion acceleration energy is low, the directivity of ions in the ion beam 2 is unstable. As a result, when the wafer 1 on the wheel 4 is mechanically scanned with the ion beam 2, the shape of the ion beam 2 on the wafer 1 differs between an inner circumferential side of the wheel 4 and an outer circumferential side thereof. With low ion acceleration energy, a critical angle for ion channeling widens. As a result, an angle between the ion beam 2 and the surface of the wafer 1 with the ion beam 2 being parallel to the rotation axis 5 of the wheel 4 approaches the channeling critical angles, and the angle between the surface of the wafer 1 and the ion beam 2 that provides a minimum in-plane deviation involves large channeling differences. To cope with this problem, the ion beam 2 is shifted to increase a tilt angle by 2 degrees in a direction that involves a smaller increase in a deviation of the angle between the surface of the wafer 1 and the ion beam 2. Although it is preferable to make the ion beam 2 parallel (0 degrees) with the rotation axis 5 of the wheel 4, the ion beam 2 may be shifted slightly to improve an in-plane uniformity of measurements and secure measurements of good reproducibility.

As shown in FIG. 22, a standard deviation on dose basis of signal strength on the wafer 1 becomes smaller and suppresses in-plane variations of signal strength further when the angle between the ion beam 2 and the rotation axis 5 of the wheel 4 is +2 degrees than when the angle is −2 degrees or when they are parallel to each other.

When the ion implanter of FIG. 1 implants ions in a wafer at a low acceleration energy, it is preferable to select an ion implantation angle that reduces a deviation of the angle between the ion beam 2 and the surface of the wafer. However, when the deviation is close to channeling critical angles, the tilt angle must be increased by several degrees to suppress in-plane variations of signal strength on the wafer and secure measurements with good reproducibility.

THIRD EXAMPLE OF ION IMPLANTATION

A third example of the ion implantation stage S20 of FIG. 9 employs an intermediate acceleration energy for the ion beam 2.

In stage S20, the ion implanter of FIG. 1 implants boron (B) ions in a wafer 1 at an acceleration energy of 30 keV. Before the ion implantation, a natural oxide film formed on the surface of the wafer 1 is removed with dilute hydrofluoric acid. In stage S30a after the ion implantation, the apparatus of FIG. 2 measures a reflected probe beam 28 from the wafer 1. At this time, when the ion beam 2 is substantially in parallel with the rotation axis 5 of the wheel 4, in-plane variations of signal strength on the wafer 1 will be small. At the time of ion implantation, however, a position of the ion beam 2 on the surface of the wafer 1 shifts slightly to deteriorate an in-plane uniformity of signal strengths on the wafer 1. As a result, in-plane variations of signal strength on the wafer 1 will not be reduced even if the ion beam 2 is substantially in parallel with the rotation axis 5.

To cope with this problem with an intermediate acceleration energy, ion implantation angle conditions that involve, for example, a tilt angle of 5 degrees and a twist angle of 15 degrees are employed. As a result, circumferential angle variations, that may occur even if the ion beam 2 is in parallel with the rotation axis 5 of the wheel 4, are reduced, an in-plane uniformity of signal strengths over the wafer 1 is improved, and measurements of good reproducibility are realized.

When the angle between the rotation axis 5 of the wheel 4 and the wafer 1 is 5 degrees, tilt and twist angles are required to satisfy conditions shown in FIG. 23. Namely, ion implanting conditions to reduce circumferential angular variations include a tilt angle of 5 degrees and a twist angle of 255 to 270 degrees. At a tilt angle of 5 degrees and a twist angle of 180 degrees, the ion beam 2 is in parallel with the rotation axis 5.

For example, boron (B) ions are implanted at an acceleration energy of 30 keV in a wafer 1 on which a natural oxide film of 8 nm thick is formed. In this case, variations in the angle between the ion beam 2 and the surface of the wafer 1 do not substantially influence the characteristics of the wafer 1 due to the presence of the oxide film. However, when the position of the ion beam 2 on the surface of the wafer 1 shifts slightly, an in-plane uniformity of signal strengths on the wafer 1 is deteriorated.

To reduce a shift of the ion beam 2, ion implantation angles are determined in consideration of the vector and spatial distribution of the ion beam 2. As a result, the in-plane uniformity of signal strengths on the surface of the wafer 1 is improved. For example, in FIG. 24, the angle between the ion beam 2 and the surface of the wafer 1 is set to +4 degrees in order to improve an in-plane uniformity of signal strengths on the surface of the wafer 1 and realize measurements of good reproducibility.

FIRST EXAMPLE OF AMORPHOUS DETERMINATION

Generally, determination of whether or not the topmost surface of a wafer is in an amorphous state after ion implantation is made by conducting Rutherford backscattering spectrometry (RBS) or by observing the wafer with a transmission electron microscope (TEM). However, it is difficult to employ RBS or TEM for in-line quality control (QC), and therefore, a skilled operator of amorphous observation must determine an amorphous state according to his or her experience and knowledge. Preparing samples for TEM observation takes a long time, and therefore, several days are sometimes needed to measure an amorphous layer forming state.

Figure 25:
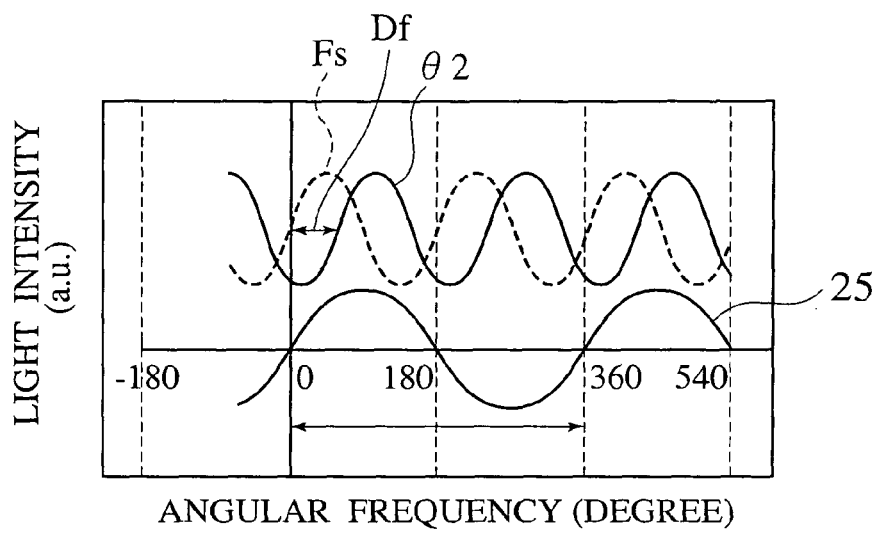
FIG. 25 is a graph showing a pump beam, a double frequency component $\theta 2$ of a reflected probe beam having a frequency twice as large as a pump beam modulation frequency, and a reference modulation component Fs according to a first example of amorphous determination.

A first example of amorphous determination according to the present invention will be explained. In stage S20 of FIG. 9, the ion implanter of FIG. 1 implants arsenic (As) ions in a wafer at an acceleration energy of 30 keV. In stage S30a after the ion implantation, the apparatus of FIG. 2 irradiates a probe beam 26 and pump beam 25 modulated at 2 kHz on the wafer 1 and measures a reflected probe beam 28. As shown in FIG. 25, a component whose frequency is twice as large as the modulation frequency of the pump beam 25 is selectively picked up from the reflected probe beam 28. The component picked up is referred to as the double frequency component $\theta2$.

A phase shift Df between the double frequency component $\theta2$ and a reference modulation Fs is monitored, and according to the phase shift Df, it is objectively determined whether or not the topmost surface of the wafer 1 is in an amorphous state. In practice, a calibration curve indicative of a relationship between an amorphous state and the double frequency component $\theta2$ is prepared in advance. By use of the calibration curve, it is possible to measure the degree of an amorphous state relative to an implanted ion dose.

Figure 26A:
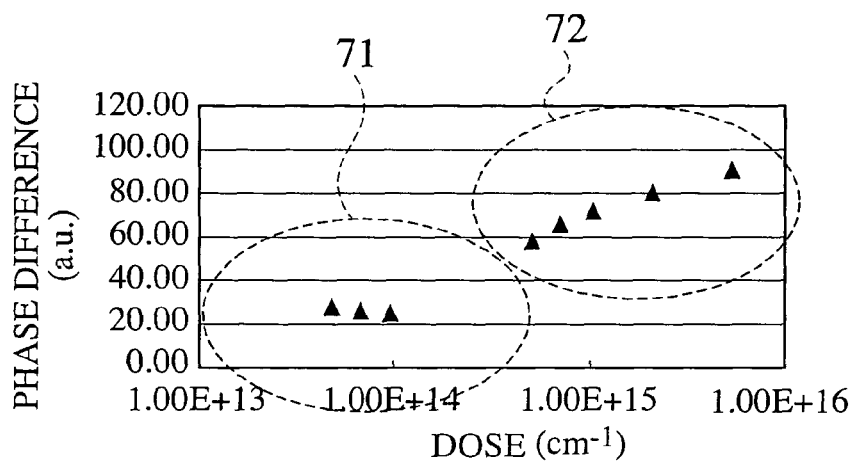
FIG. 26A is a graph showing a relationship between phase shifts Df (FIG. 25) and implanted ion doses.
Figure 26B:
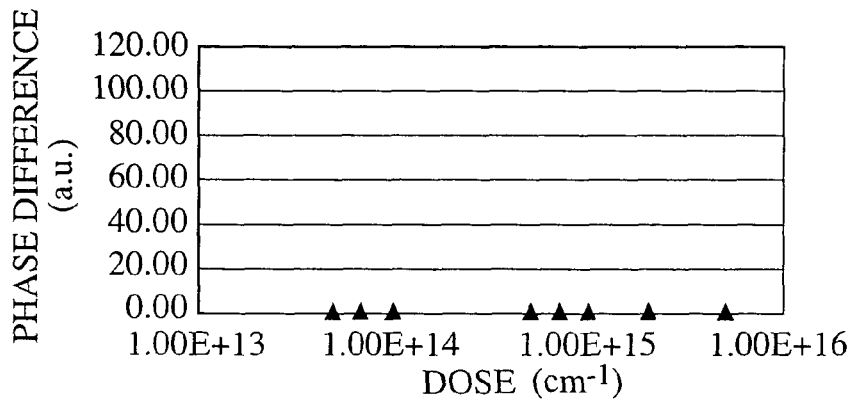
FIG. 26B is a graph showing a relationship between phase shifts of reflected probe beam components that are synchronous with a pump beam modulation frequency and implanted ion doses.

When an implanted ion dose is relatively small as shown in FIG. 26A, the phase shift Df is small forming no amorphous layer. On the other hand, when the implanted ion dose is relatively large, the phase shift Df becomes larger and forms an amorphous layer. Consequently, a calibration curve indicative of a relationship between a first region 71 involving small phase shifts and a second region 72 involving large phase shifts, to determine whether or not there is an amorphous layer. As shown in FIG. 26B, a component among the reflected probe beam 28 that is synchronous with the modulation frequency of the pump beam 25 causes no phase shift irrespective of an implanted ion dose.

As explained above, an implanted ion dose is measured with the in-line QC unit shown in FIG. 2, and according to the measured dose, it is determined whether or not an amorphous layer is formed in the topmost surface of the wafer 1 at the time of ion implantation (stage S20). As a result, a product development site can speedily find an implanted ion dose to form an amorphous layer, and the development of products can be promoted. For example, when the dose of implant ions or a current rate fluctuates to cause insufficient formation of amorphous layer, it is possible to quickly detect the insufficient amorphous state according to the first example of amorphous determination and manage the situation.

Figure 27:
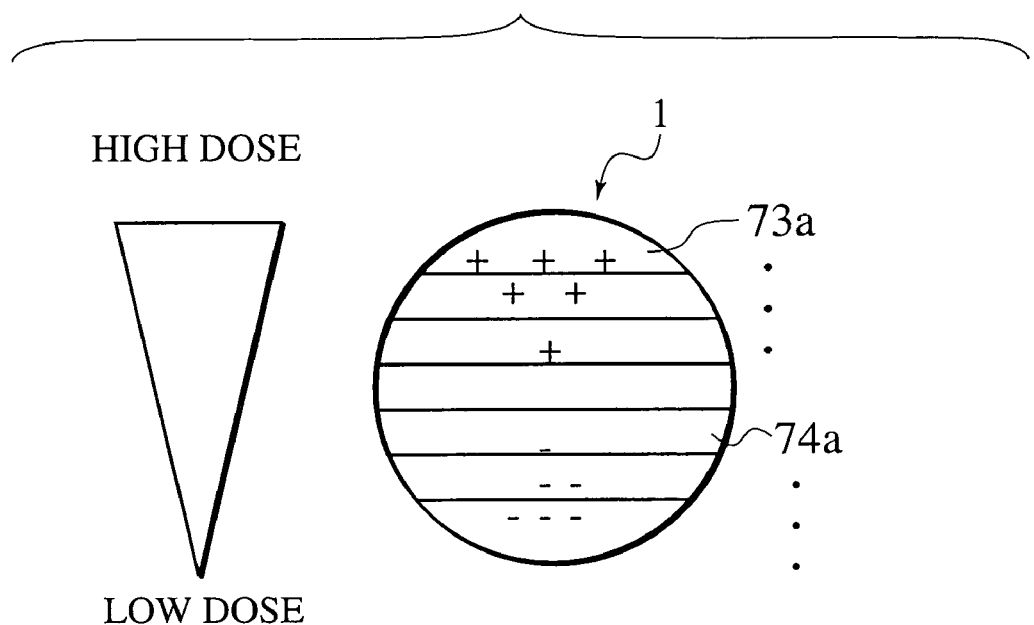
FIG. 27 is a plan view showing a wafer surface having stepwise high and low implanted ion concentration regions.

In FIG. 27, the surface of a wafer 1 is stepwise divided into high-concentration ion implanted regions 73a and the like and low-concentration ion implanted regions 74a and the like. For each of these regions 73a and 74a in the surface of the wafer 1, a double frequency component $\theta2$ is measured. Correlation between the double frequency components $\theta2$ and signal strengths to form amorphous layers is obtained in advance. The correlation is used to find an implanted ion dose to form an amorphous state from the value of a double frequency component $\theta2$. Only a single wafer is sufficient to find an implanted ion dose to form an amorphous state. An implanted ion distribution in the surface of a wafer is not required to be univocal. Ion implanted concentrations in the surface of a wafer may be changed not only in a stepwise manner but also in a continuous manner.

SECOND EXAMPLE OF AMORPHOUS DETERMINATION

The batch-type ion implanter of FIG. 1 is employed to implant $BF_2$ ions, As ions, and Ge ions in wafers in various doses. The apparatus of FIG. 2 is employed to measure in-plane signal strength distributions in the surfaces of the wafers. It is possible to detect on each wafer an amorphous state at a position where the trend of the in-plane distribution changes. Namely, the presence of an amorphous state can be determined according to a change in the in-plane distribution of intensities of a reflected probe beam 28. Consequently, the need for preparation of calibration curves can be eliminated.

Figure 28:
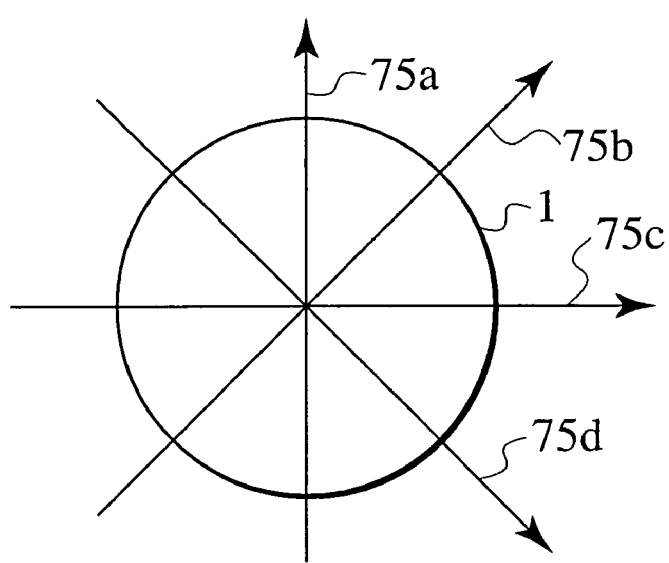
FIG. 28 is a plan view showing a wafer surface with signal strength measuring directions crossing the center of the wafer surface according to a second example of amorphous determination.

An in-plane distribution of signal strengths on the surface of a wafer involves a two-dimensional distribution and one-dimensional distributions. For example, as shown in FIG. 28, signal strengths are measured or line-scanned in directions 75a to 75d crossing the center of a wafer 1, and trends of signal strength distributions in the directions 75a to 75d are observed. With different ion implantation doses, such trends of signal strength distributions are observed. An amorphous state in a wafer is detectable along a border where the trend of signal strength distribution changes. As a result, the need for preparation of calibration curves can be eliminated.

An ion implantation dose that forms an amorphous state in a wafer depends on the temperature of the wafer at ion implantation. In the first and second examples of amorphous determination, an ion implantation dose that forms an amorphous state may be measured for each wafer temperature in advance. The measured data is used to indirectly estimate the temperature of a wafer at ion implantation. This technique is applicable to quality control (QC) when trouble occurs on a cooling mechanism of the ion implanter.

An ion implantation dose that forms an amorphous state depends on a current rate of the ion beam 2 for ion implantation. Accordingly, in the first and second examples of amorphous determination, an ion implantation dose that forms an amorphous state may be measured for each current rate of the ion beam 2 in advance, so that it may be used to detect a beam current difference of the ion beam 2 at ion implantation.

OTHER EMBODIMENTS

Although the present invention has been explained in connection with the embodiments, modifications, and examples, it must be understood that the descriptions and accompanying drawings of this specification are not restrictive to the present invention. It will be apparent for those skilled in the art that the disclosure of the present invention allows other modifications, embodiments, and applications.

For example, it is possible to employ the ion implanter of FIG. 1 to implant ions in wafers without horizontally moving the rotation axis 5 of the wheel 4 relative to a rotation plane of the wheel 4 from a ground state. In this case, mechanical fluctuations in the wheel 4 are reduced, an in-plane uniformity of microdefects in the surface of each wafer is improved, and an in-plane uniformity of signal strengths in the surface of each wafer is improved.

Any one of the apparatuses for evaluating semiconductor material of FIGS. 2 and 15 may be arranged in a manufacturing line of semiconductor devices, so that the apparatus of FIG. 2 and 15 may serve as an in-line monitor for inspecting processes including an ion implantation process.

In FIG. 9, an annealing stage may be inserted between the ion implantation stage S20 and the inspection stage S30. In this case, any one of the apparatuses for evaluating semiconductor material of FIGS. 2 and 15 can evaluate the depths of pn junctions after the annealing stage.

The ion implantation stage S20 of FIG. 9 is an example of a process to be inspected by the inspection stage S30. The process to be inspected according to the present invention is not limited to the ion implantation stage S20. It may be a semiconductor film or metal film forming stage. In this case, any one of the apparatuses for evaluating semiconductor material of FIGS. 2 and 15 evaluates the thickness of the semiconductor film or metal film.

It must be understood, therefore, that the present invention can be embodied in other forms not specified herein. The present invention is limited only by specific inventive items disclosed herein and defined in appended claims.

As explained above, the embodiments of the present invention provide the apparatuses for and method of evaluating semiconductor material capable of conducting highly accurate measurements of good reproducibility.

What is claimed is:

1. A method for evaluating semiconductor material, comprising:

irradiating a pump beam modulated at a modulation frequency on a semiconductor wafer;

irradiating a probe beam on the semiconductor wafer;

measuring an intensity of a reflection of the probe beam from the semiconductor wafer while irradiating the pump beam and the probe beam on the semiconductor wafer;

finding a first functional form indicating a relation between a first elapsed time period from a time when ions were implanted into the semiconductor wafer to a time when the intensity of the reflection was measured and intensity changes of the reflection; and finding an intensity of the reflection just after the ions were implanted into the semiconductor wafer according to the intensity of the reflection measured, the first elapsed time period, and the first functional form.

2. The method of claim 1, further comprising:

finding a second functional form indicating a relation between a second elapsed time period from a time when irradiation of the probe beam on the semiconductor wafer was begun to the time when the intensity of the reflection was measured and said intensity changes of the reflection; and finding an intensity of the reflection just after irradiation of the probe beam on the semiconductor wafer was begun according to the second functional form, wherein the finding an intensity of the reflection just after the ions were implanted into the semiconductor wafer, is carried out according to the intensity of the reflection just after irradiation of the probe beam on the semiconductor wafer was begun, the first elapsed time period, and the first functional form.

3. The method of claim 2, wherein the second functional form is expressed by adding up a plurality of terms including a logarithm of the second elapsed time period.

4. The method of claim 1, wherein the first functional form is expressed by adding up a plurality of terms including a logarithm of the first elapsed time period.

* * * * *